United States Patent
Cha et al.

(10) Patent No.: US 11,482,677 B2
(45) Date of Patent: Oct. 25, 2022

(54) COMPOUND AND ORGANIC ELECTRONIC DEVICE COMPRISING SAME

(71) Applicant: LG Chem, Ltd., Seoul (KR)

(72) Inventors: Yongbum Cha, Daejeon (KR); Sung Kil Hong, Daejeon (KR); Jungoh Huh, Daejeon (KR); Jin Joo Kim, Daejeon (KR)

(73) Assignee: LG Chem, Ltd.

( * ) Notice: Subject to any disclaimer, the term of this patent is extended or adjusted under 35 U.S.C. 154(b) by 413 days.

(21) Appl. No.: 15/742,604

(22) PCT Filed: Jan. 9, 2017

(86) PCT No.: PCT/KR2017/000245
§ 371 (c)(1),
(2) Date: Jan. 8, 2018

(87) PCT Pub. No.: WO2017/119792
PCT Pub. Date: Jul. 13, 2017

(65) Prior Publication Data
US 2018/0123042 A1 May 3, 2018

(30) Foreign Application Priority Data

Jan. 7, 2016 (KR) ........................ 10-2016-0002055

(51) Int. Cl.
| | |
|---|---|
| H01L 51/00 | (2006.01) |
| C07D 333/76 | (2006.01) |
| C07D 307/91 | (2006.01) |
| C09K 11/06 | (2006.01) |
| H01L 51/50 | (2006.01) |
| C07F 7/30 | (2006.01) |
| C07F 7/08 | (2006.01) |

(Continued)

(52) U.S. Cl.
CPC .......... *H01L 51/006* (2013.01); *C07C 211/54* (2013.01); *C07C 211/61* (2013.01);
(Continued)

(58) Field of Classification Search
CPC . C07C 13/567; C07C 2603/18; C07C 211/54; C07C 211/61; C07D 333/76;
(Continued)

(56) References Cited

U.S. PATENT DOCUMENTS

2004/0251816 A1   12/2004  Leo et al.
2006/0166034 A1*  7/2006   Saitoh ................... C07C 211/61
                                                                  428/690

(Continued)

FOREIGN PATENT DOCUMENTS

CN    104364245 A    2/2015
JP    2015120692 A   7/2015
(Continued)

OTHER PUBLICATIONS

Chinese Search Report for Application No. CN 201780002417.3 dated Sep. 16, 2019, 2 pages.

(Continued)

*Primary Examiner* — Andrew K Bohaty
*Assistant Examiner* — Jenna N Chandhok
(74) *Attorney, Agent, or Firm* — Lerner, David, Littenberg, Krumholz & Mentlik, LLP

(57) ABSTRACT

The present specification relates to a compound and an organic electronic device including the same.

6 Claims, 1 Drawing Sheet

(51) Int. Cl.
  *C07C 211/61* (2006.01)
  *C07C 211/54* (2006.01)
(52) U.S. Cl.
  CPC ......... *C07D 307/91* (2013.01); *C07D 333/76* (2013.01); *C07F 7/0805* (2013.01); *C07F 7/30* (2013.01); *C09K 11/06* (2013.01); *H01L 51/00* (2013.01); *H01L 51/0061* (2013.01); *H01L 51/50* (2013.01); *C07C 2603/18* (2017.05); *C07C 2603/26* (2017.05); *H01L 51/0058* (2013.01); *H01L 51/0073* (2013.01); *H01L 51/0074* (2013.01); *H01L 51/5012* (2013.01); *H01L 51/5056* (2013.01); *H01L 51/5088* (2013.01); *H01L 51/5096* (2013.01)
(58) Field of Classification Search
  CPC . C07D 307/91; H01L 51/0058; H01L 51/006; H01L 51/0073; H01L 51/0074; H01L 51/0061; H01L 2211/1014
  See application file for complete search history.

(56) References Cited

U.S. PATENT DOCUMENTS

| | | |
|---|---|---|
| 2010/0108997 A1 | 5/2010 | Kim et al. |
| 2012/0181922 A1* | 7/2012 | Kawamura ......... H01L 51/0052 313/504 |
| 2015/0155491 A1 | 6/2015 | Mujica-Fernaud et al. |
| 2016/0043316 A1 | 2/2016 | Takada et al. |
| 2016/0372665 A1* | 12/2016 | Takada ................ H01L 51/0061 |
| 2017/0018710 A1* | 1/2017 | Mujica-Fernaud ... C07C 211/54 |

FOREIGN PATENT DOCUMENTS

| | | |
|---|---|---|
| KR | 20130096334 A | 8/2013 |
| KR | 20150023657 A | 3/2015 |
| KR | 20150096020 A | 8/2015 |
| KR | 20160019839 A | 2/2016 |
| KR | 20160120609 A | 10/2016 |
| TW | 201030122 A | 8/2010 |
| WO | 2003012890 A2 | 2/2003 |

OTHER PUBLICATIONS

STN Registry, Feb. 13, 2015.
Search report from International Application No. PCT/KR2017/000245 is an English language counterpart.
Taiwanese Search Report for Application No. 107105751 dated Aug. 6, 2018.

* cited by examiner

[Figure 1]
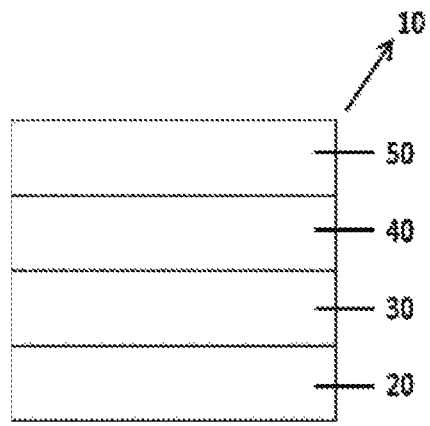
[Figure 2]
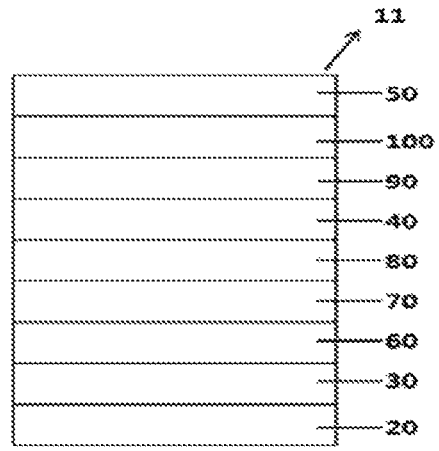

COMPOUND AND ORGANIC ELECTRONIC DEVICE COMPRISING SAME

CROSS-REFERENCE TO RELATED APPLICATIONS

The present application is a national phase entry under 35 U.S.C. § 371 of International Application No. PCT/KR2017/000245 filed Jan. 9, 2017, which claims priority from Korean Patent Application No. 10-2016-0002055 filed Jan. 7, 2016, all of which are incorporated herein by reference.

TECHNICAL FIELD

The present specification relates to a compound and an organic electronic device including the same.

BACKGROUND ART

Representative examples of an organic electronic device include an organic light emitting device. In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

Such an organic light emitting device has been known to have characteristics such as self-emission, high brightness, high efficiency, a low driving voltage, a wide viewing angle, high contrast, and a quick responsiveness.

In an organic light emitting device, materials used as an organic material layer may be classified into a light emitting material and a charge transporting material, for example, a hole injection material, a hole transporting material, an electron transporting material, an electron injection material, and the like depending on the function. Further, the light emitting materials may be divided into blue, green, and red light emitting materials depending on the light emitting color, and into yellow and orange light emitting materials required for implementing a much better natural color. Meanwhile, when only one material is used as the light emitting material, there occur problems in that a maximum light emitting wavelength moves to a long wavelength due to an interaction between molecules, color purity deteriorates, or the efficiency of the device is reduced due to a light emission diminution effect, and accordingly, a host/dopant-based material may be used as the light emitting material in order to increase color purity and increase light emitting efficiency through an energy transfer.

In order for an organic light emitting device to sufficiently exhibit the above-described excellent characteristics, materials which form an organic material layer in the device, for example, a hole injection material, a hole transporting material, a light emitting material, an electron transporting material, an electron injection material, and the like first need to be supported by stable and efficient materials, but stable and efficient materials for an organic material layer for an organic light emitting device have not been sufficiently developed up to now. Therefore, there is a continuous need for developing a new material, and the need for developing such materials also applies to the above-described other organic electronic devices.

CITATION LIST

Patent Document

International Publication No. 2003-012890

DISCLOSURE

Technical Problem

The present specification has been made in an effort to provide a compound and an organic electronic device including the same.

Technical Solution

The present specification provides a compound represented by the following Chemical Formula 1.

[Chemical Formula 1]

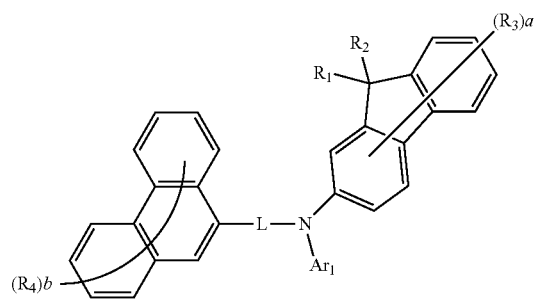

In Chemical Formula 1,

L is a direct bond; or a substituted or unsubstituted phenylene group, $R_1$ to $R_4$ are the same as or different from each other, and are each independently hydrogen; deuterium; a halogen group; or a substituted or unsubstituted alkyl group, a is an integer from 1 to 7, b is an integer from 1 to 9, when a is 2 or more, a plurality of $R_3$'s is the same as or different from each other, when b is 2 or more, a plurality of $R_4$'s is the same as or different from each other, $Ar_1$ may be represented by $-(L_1)_m-Ar_2$ or the following Chemical Formula 2, $L_1$ is a direct bond; a substituted or unsubstituted phenylene group; a substituted or unsubstituted biphenylene group; a substituted or unsubstituted naphthylene group; or a substituted or unsubstituted divalent fluorene group, m is an integer from 0 to 3, when m is 2 or more, a plurality of $L_1$'s is the same as or different from each other, Ar$_2$ is deuterium; a halogen group; a cyano group; an alkyl group; an alkoxy group; an alkylsilyl group; or a substituted or unsubstituted C$_6$ to c$_{30}$ aryl group,

[Chemical Formula 2]

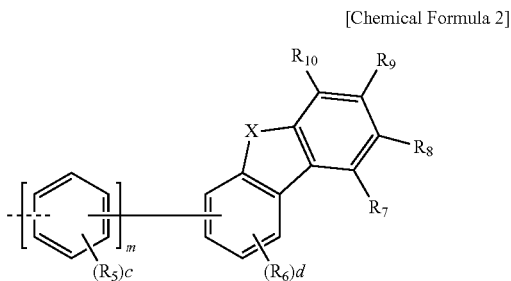

in Chemical Formula 2,

------- is a moiety which is bonded to N of Chemical Formula 1,

X is S, O, or SO$_2$, m is the same as that defined in Chemical Formula 1,

R$_5$ to R$_{10}$ are the same as or different from each other, and are each independently hydrogen; deuterium; a halogen group; a substituted or unsubstituted alkyl group; a substituted or unsubstituted aryl group; or a substituted or unsubstituted heteroaryl group, c is an integer from 1 to 4, d is an integer from 1 to 3, when c is 2 or more, a plurality of R$_5$'s is the same as or different from each other, and when d is 2 or more, a plurality of R$_6$'s is the same as or different from each other.

Further, the present specification provides an organic electronic device including: a first electrode; a second electrode disposed to face the first electrode; and an organic material layer having one or more layers disposed between the first electrode and the second electrode, in which one or more layers of the organic material layer include the above-described compound.

Advantageous Effects

The compound according to an exemplary embodiment of the present specification is used for an organic electronic device including an organic light emitting device, and thus may lower the driving voltage of the organic electronic device and improve the light efficiency thereof, and enhance service life characteristics of the device due to thermal stability of the compound.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides the compound represented by Chemical Formula 1.

According to an exemplary embodiment of the present specification, the compound represented by Chemical Formula 1 may have the core structure and thus have low voltage, high efficiency, and long service life characteristics. Specifically, the phenanthrene in a core structure of Chemical Formula 1 contains more abundant electrons than benzene and naphthalene, and the core structure may increase the hole mobility as compared to benzene, naphthalene, and phenanthrene by including an amine group in which a fluorene group is directly substituted, and thus has better hole transporting characteristics than the NPB in the related art. Further, the core structure may have excellent hole injection characteristics by increasing the HOMO level to lower the hole injection barrier at the interface of a positive electrode and ITO.

Examples of the substituents in the present specification will be described below, but are not limited thereto.

In the present specification, ------ or

means a moiety to be linked.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; an alkyl group; a cycloalkyl group; an alkoxy group; an alkylsilyl group; a silyl group; an aryl group; and a heteroaryl group including one or more of N, O, S, Se, and Si atoms, being substituted with a substituent to which two or more substituents among the substituents exemplified are linked, or having no substituent.

In the present specification, examples of a halogen group include fluorine, chlorine, bromine or iodine.

In the present specification, an alkyl group may be straight or branched, and the number of carbon atoms thereof is not particularly limited, but is preferably 1 to 40. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, a cycloalkyl group is not particularly limited, but has preferably 3 to 40 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, a silyl group includes Si and is a substituent to which the Si atom is directly linked as a radical, and is represented by $-SiR_{104}R_{105}R_{106}$, and $R_{104}$ to $R_{106}$ are the same as or different from each other, and may be each independently a substituent composed of at least one of hydrogen; deuterium; a halogen group; an alkyl group; an alkenyl group; an alkoxy group; a cycloalkyl group; an aryl group; and a heterocyclic group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, an alkylsilyl group is a silyl group in which an alkyl group is substituted, and may be selected from the examples of the silyl group.

In the present specification, when an aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 50. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the group may be

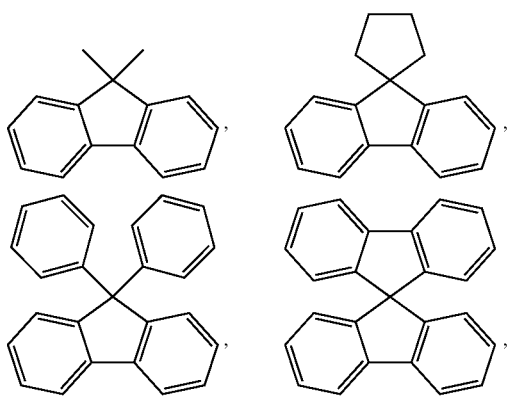

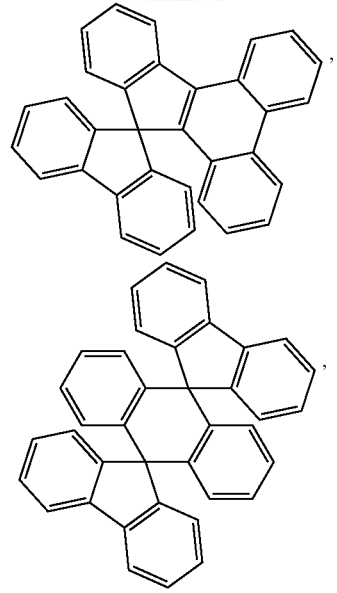

and the like, but is not limited thereto.

In the present specification, a heteroaryl group is a heterocyclic group including one or more of N, O, S, Si, and Se as a heteroatom, and the number of carbon atoms thereof is not particularly limited, but is preferably 2 to 60. Examples of the heteroaryl group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a dibenzofuranyl group, and the like, but are not limited thereto.

In the present specification, an aromatic ring group may be monocyclic or polycyclic, and may be selected from the examples of the aryl group, except for the aromatic ring group which is not a monovalent group.

In the present specification, an arylene group means a group having two bonding positions in an aryl group, that is, a divalent group. The above-described description on the aryl group may be applied to the arylene group, except for a divalent arylene group.

According to an exemplary embodiment of the present specification, L is a direct bond; or a substituted or unsubstituted phenylene group.

According to an exemplary embodiment of the present specification, L is a direct bond or a phenylene group.

According to an exemplary embodiment of the present specification, L is a direct bond.

According to an exemplary embodiment of the present specification, L is a phenylene group.

According to an exemplary embodiment of the present specification, $R_1$ to $R_4$ are the same as or different from each other, and are each independently hydrogen; deuterium; a halogen group; or a substituted or unsubstituted alkyl group.

According to an exemplary embodiment of the present specification, $R_1$ to $R_4$ are hydrogen.

According to an exemplary embodiment of the present specification, $R_1$ and $R_2$ are the same as or different from each other, and are each independently a $C_1$ to $C_{10}$ alkyl group.

According to an exemplary embodiment of the present specification, $R_1$ and $R_2$ are the same as or different from each other, and are each independently a methyl group or an ethyl group.

According to an exemplary embodiment of the present specification, $R_1$ and $R_2$ are a methyl group.

According to an exemplary embodiment of the present specification, $R_3$ and $R_4$ are hydrogen.

According to an exemplary embodiment of the present specification, $Ar_1$ may be represented by -$(L_1)_m$-$Ar_2$ or the following Chemical Formula 2.

According to an exemplary embodiment of the present specification, $L_1$ is a direct bond; a substituted or unsubstituted phenylene group; a substituted or unsubstituted biphenylene group; a substituted or unsubstituted naphthylene group; or a substituted or unsubstituted divalent fluorene group.

According to an exemplary embodiment of the present specification, $L_1$ is a direct bond.

According to an exemplary embodiment of the present specification, $L_1$ is a phenylene group.

According to an exemplary embodiment of the present specification, $L_1$ is a biphenylene group.

According to an exemplary embodiment of the present specification, $L_1$ is a naphthylene group.

According to an exemplary embodiment of the present specification, $L_1$ is a divalent fluorene group.

According to an exemplary embodiment of the present specification, m is an integer from 0 to 3, and when m is 2 or more, a plurality of $L_1$'s is the same as or different from each other.

According to an exemplary embodiment of the present specification, $Ar_2$ is deuterium; a halogen group; a cyano group; an alkyl group; an alkoxy group; an alkylsilyl group; or a substituted or unsubstituted $C_6$ to $c_{30}$ aryl group.

According to an exemplary embodiment of the present specification, $Ar_2$ is deuterium; a halogen group; a cyano group; a $C_1$ to $C_{10}$ alkyl group; a $C_1$ to $C_{10}$ alkoxy group; or a $C_1$ to $C_{10}$ alkylsilyl group.

According to an exemplary embodiment of the present specification, $Ar_2$ is deuterium, a halogen group, a cyano group, a methyl group, an ethyl group, a propyl group, an i-propyl group, a butyl group, a t-butyl group, a methoxy group, an ethoxy group, or a trimethylsilyl group.

According to an exemplary embodiment of the present specification, $Ar_1$ is a -phenylene-naphthyl group, a -phenylene-phenanthrenyl group, a -naphthylene-phenyl group, a -naphthylene-naphthyl group, a -fluorenylene-dimethyl group, a -phenylene-fluorenylene-dimethyl group, a -naphthylene-fluorenylene-dimethyl group, a -phenylene-phenylene-naphthyl group, a -phenylene-phenylene-phenanthrenyl group, a -phenylene-phenylene-methyl group, a -phenylene-phenylene-(t-butyl) group, a -phenylene-phenylene-cyano group, a -phenylene-phenylene-fluorine group, a -phenylene-phenylene-methoxy group, a -phenylene-phenylene-trimethylsilyl group, a -phenylene-fluorenylene-dimethyl group, a -(9,9-dimethylfluorenyl) lene-phenyl group, a -(9,9-dimethylfluorenyl)lene-naphthyl group, or a -(9,9-dimethylfluorenyl) lene-phenanthrenyl group.

According to an exemplary embodiment of the present specification, $Ar_2$ is a substituted or unsubstituted $C_6$ to $C_{30}$ aryl group.

According to an exemplary embodiment of the present specification, $Ar_2$ is a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, or a substituted or unsubstituted fluorenyl group.

According to an exemplary embodiment of the present specification, $Ar_2$ is an alkoxy group, a cyano group, a halogen group, a silyl group, an alkyl group, or a phenyl group in which an aryl group is substituted or unsubstituted.

According to an exemplary embodiment of the present specification, $Ar_2$ is methoxy, a cyano group, fluorine, a silyl group, a methyl group, an ethyl group, an isopropyl group, a tert-butyl group, a phenyl group, a biphenyl group, a naphthyl group, a phenanthryl group, or a phenyl group in which a fluorenyl group is substituted or unsubstituted.

According to an exemplary embodiment of the present specification, $Ar_2$ is a phenyl group.

According to an exemplary embodiment of the present specification, $Ar_2$ is an alkoxy group, a cyano group, a halogen group, a silyl group, an alkyl group, or a biphenyl group in which an aryl group is substituted or unsubstituted.

According to an exemplary embodiment of the present specification, $Ar_2$ is methoxy, a cyano group, fluorine, a silyl group, a methyl group, an ethyl group, an isopropyl group, a tert-butyl group, a phenyl group, a biphenyl group, a naphthyl group, a phenanthryl group, or a biphenyl group in which a fluorenyl group is substituted or unsubstituted.

According to an exemplary embodiment of the present specification, $Ar_2$ is a biphenyl group.

According to an exemplary embodiment of the present specification, $Ar_2$ is an alkoxy group, a cyano group, a halogen group, a silyl group, an alkyl group, or a naphthyl group in which an aryl group is substituted or unsubstituted.

According to an exemplary embodiment of the present specification, $Ar_2$ is methoxy, a cyano group, fluorine, a silyl group, a methyl group, an ethyl group, an isopropyl group, a tert-butyl group, a phenyl group, a biphenyl group, a naphthyl group, a phenanthryl group, or a naphthyl group in which a fluorenyl group is substituted or unsubstituted.

According to an exemplary embodiment of the present specification, $Ar_2$ is a naphthyl group.

According to an exemplary embodiment of the present specification, $Ar_2$ is an alkoxy group, a cyano group, a halogen group, a silyl group, an alkyl group, or a terphenyl group in which an aryl group is substituted or unsubstituted.

According to an exemplary embodiment of the present specification, $Ar_2$ is methoxy, a cyano group, fluorine, a silyl group, a methyl group, an ethyl group, an isopropyl group, a tert-butyl group, a phenyl group, a biphenyl group, a naphthyl group, a phenanthryl group, or a terphenyl group in which a fluorenyl group is substituted or unsubstituted.

According to an exemplary embodiment of the present specification, $Ar_2$ is a terphenyl group.

According to an exemplary embodiment of the present specification, $Ar_2$ is an alkoxy group, a cyano group, a halogen group, a silyl group, an alkyl group, or a phenanthryl group in which an aryl group is substituted or unsubstituted.

According to an exemplary embodiment of the present specification, $Ar_2$ is methoxy, a cyano group, fluorine, a silyl group, a methyl group, an ethyl group, an isopropyl group, a tert-butyl group, a phenyl group, a biphenyl group, a naphthyl group, a phenanthryl group, or a phenanthryl group in which a fluorenyl group is substituted or unsubstituted.

According to an exemplary embodiment of the present specification, $Ar_2$ is a phenanthryl group.

According to an exemplary embodiment of the present specification, $Ar_2$ is an alkoxy group, a cyano group, a halogen group, a silyl group, an alkyl group, or a fluorenyl group in which an aryl group is substituted or unsubstituted.

According to an exemplary embodiment of the present specification, $Ar_2$ is methoxy, a cyano group, fluorine, a silyl group, a methyl group, an ethyl group, an isopropyl group, a tert-butyl group, a phenyl group, a biphenyl group, a naphthyl group, a phenanthryl group, or a fluorenyl group in which a fluorenyl group is substituted or unsubstituted.

According to an exemplary embodiment of the present specification, $Ar_2$ is a fluorenyl group.

According to an exemplary embodiment of the present specification, $Ar_1$ may be represented by the following Chemical Formula 2.

[Chemical Formula 2]

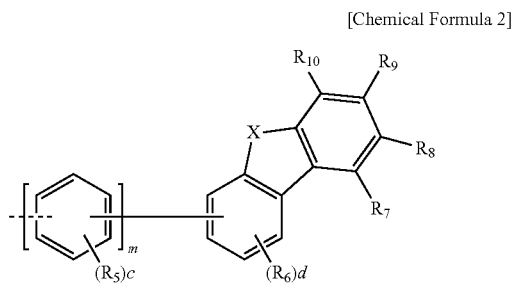

In Chemical Formula 2,

- - - - - - - is a moiety which is bonded to N of Chemical Formula 1,

X is S, O, or $SO_2$, m is the same as that defined in Chemical Formula 1, $R_5$ to $R_{10}$ are the same as or different from each other, and are each independently hydrogen; deuterium; a halogen group; a substituted or unsubstituted alkyl group; a substituted or unsubstituted aryl group; or a substituted or unsubstituted heteroaryl group, c is an integer from 1 to 4, d is an integer from 1 to 3, when c is 2 or more, a plurality of $R_5$'s is the same as or different from each other, and when d is 2 or more, a plurality of $R_6$'s is the same as or different from each other.

According to an exemplary embodiment of the present specification, Chemical Formula 2 may be represented by the following Chemical Formula 2-1.

[Chemical Formula 2-1]

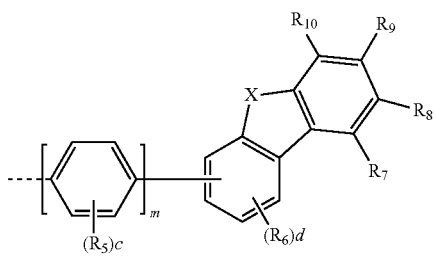

In Chemical Formula 2-1,

- - - - - - - is a moiety which is bonded to N of Chemical Formula 1, and

X, m, c, d, and $R_5$ to $R_{10}$ are the same as those defined in Chemical Formula 2.

According to an exemplary embodiment of the present specification, X is S.

According to an exemplary embodiment of the present specification, X is O.

According to an exemplary embodiment of the present specification, X is $SO_2$.

According to an exemplary embodiment of the present specification, $R_5$ to $R_{10}$ are the same as or different from each other, and are each independently a substituted or unsubstituted aryl group.

According to an exemplary embodiment of the present specification, $R_5$ to $R_{10}$ are the same as or different from each other, and are each independently a substituted or unsubstituted phenyl group; a substituted or unsubstituted biphenyl group; a substituted or unsubstituted naphthyl group; a substituted or unsubstituted anthracenyl group, a substituted or unsubstituted phenanthrenyl group, or a substituted or unsubstituted fluorenyl group.

According to an exemplary embodiment of the present specification, $R_5$ to $R_{10}$ are the same as or different from each other, and are each independently a phenyl group, a biphenyl group, a naphthyl group, an anthracenyl group, a phenanthryl group, or a fluorenyl group.

According to an exemplary embodiment of the present specification, $R_6$ is a substituted or unsubstituted aryl group.

According to an exemplary embodiment of the present specification, $R_6$ is a substituted or unsubstituted phenyl group; a substituted or unsubstituted biphenyl group; a substituted or unsubstituted naphthyl group; a substituted or unsubstituted anthracenyl group; a substituted or unsubstituted phenanthrenyl group, or a substituted or unsubstituted fluorenyl group.

According to an exemplary embodiment of the present specification, $R_6$ is a phenyl group.

According to an exemplary embodiment of the present specification, $R_6$ is a biphenyl group.

According to an exemplary embodiment of the present specification, $R_6$ is a naphthyl group.

According to an exemplary embodiment of the present specification, $R_5$ to $R_{10}$ are hydrogen.

According to an exemplary embodiment of the present specification, $R_5$ to $R_7$, $R_9$, and $R_{10}$ are hydrogen.

According to an exemplary embodiment of the present specification, the compound of Chemical Formula 1 may be any one selected from the following structures.

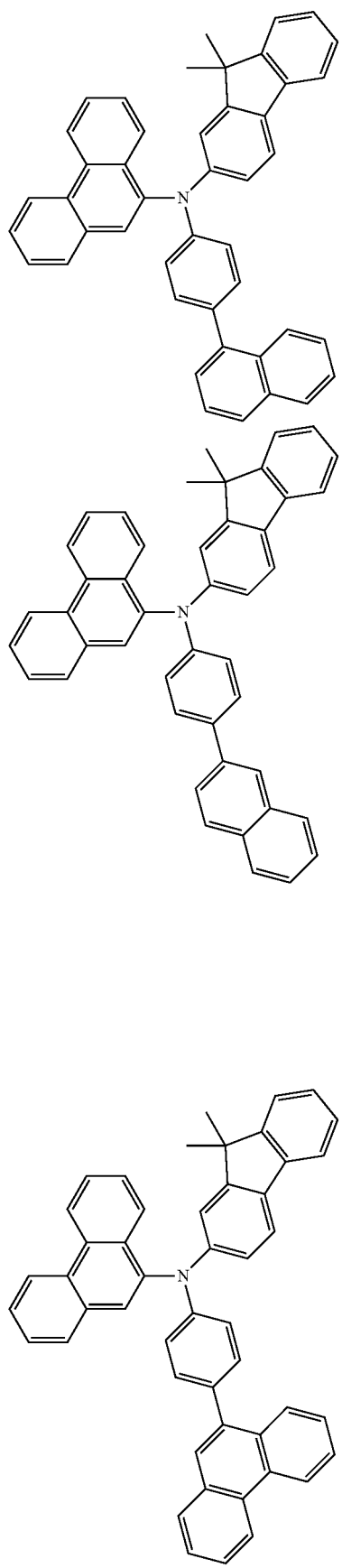
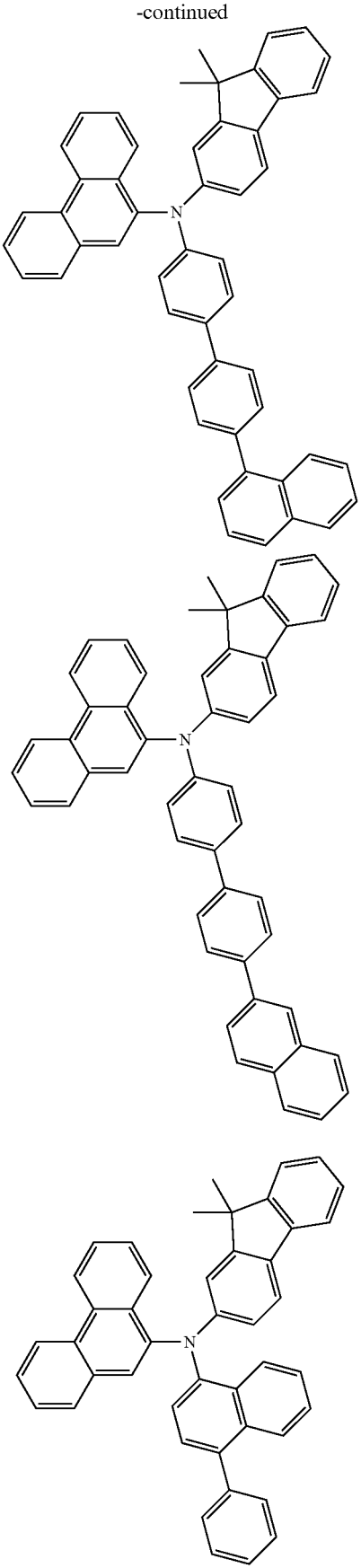

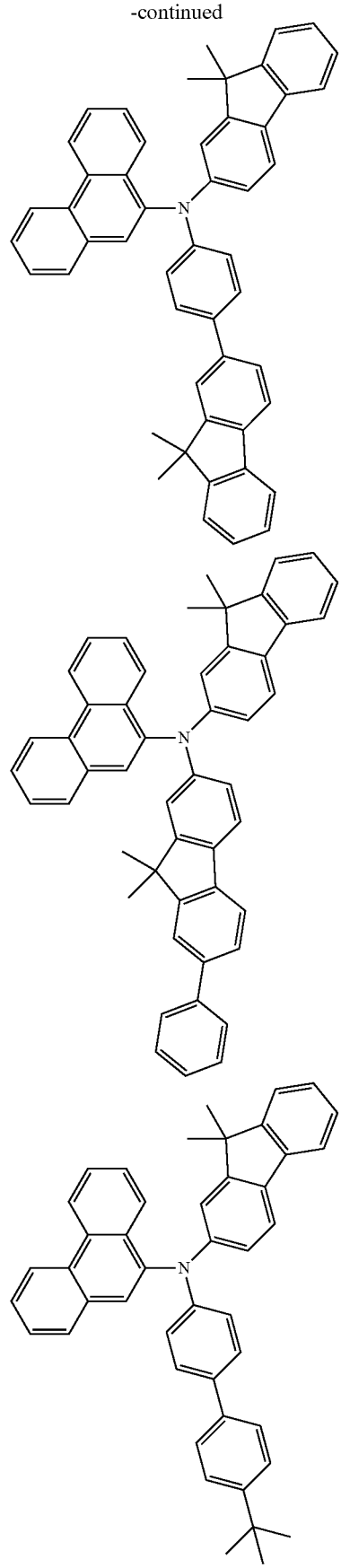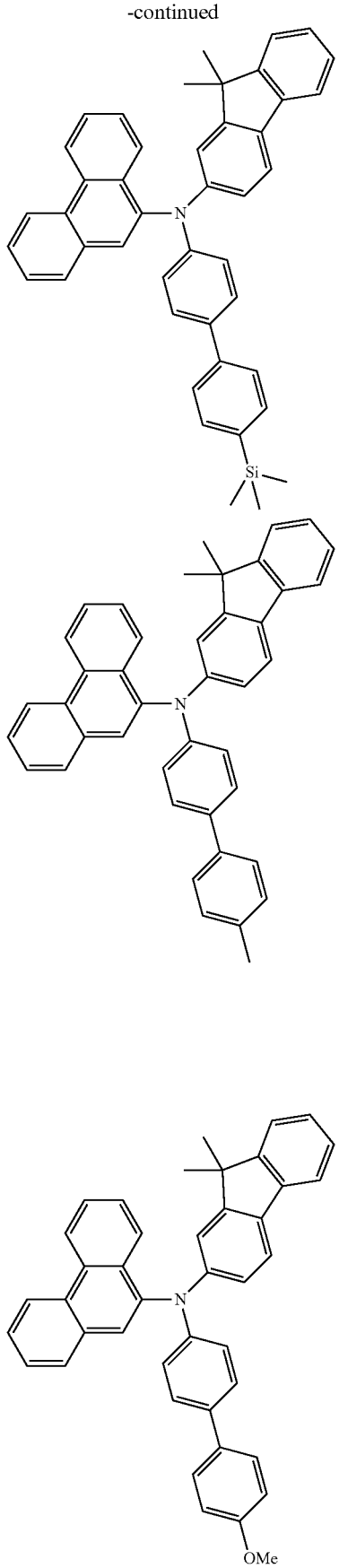

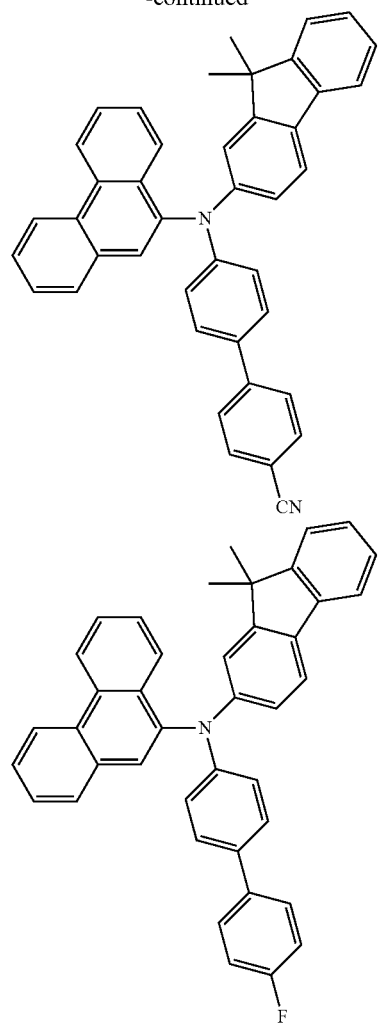
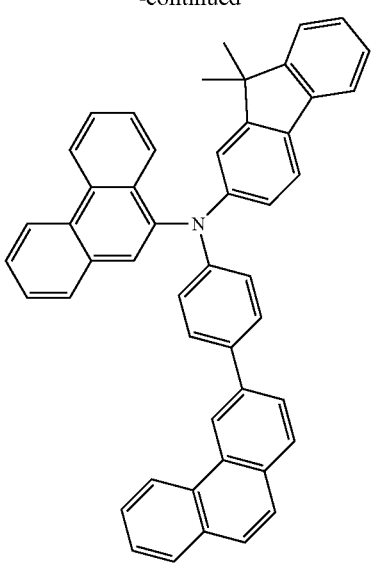
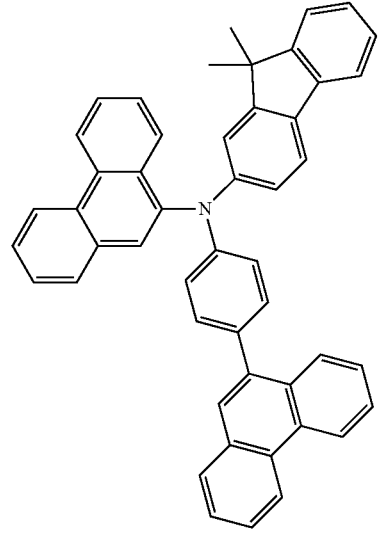

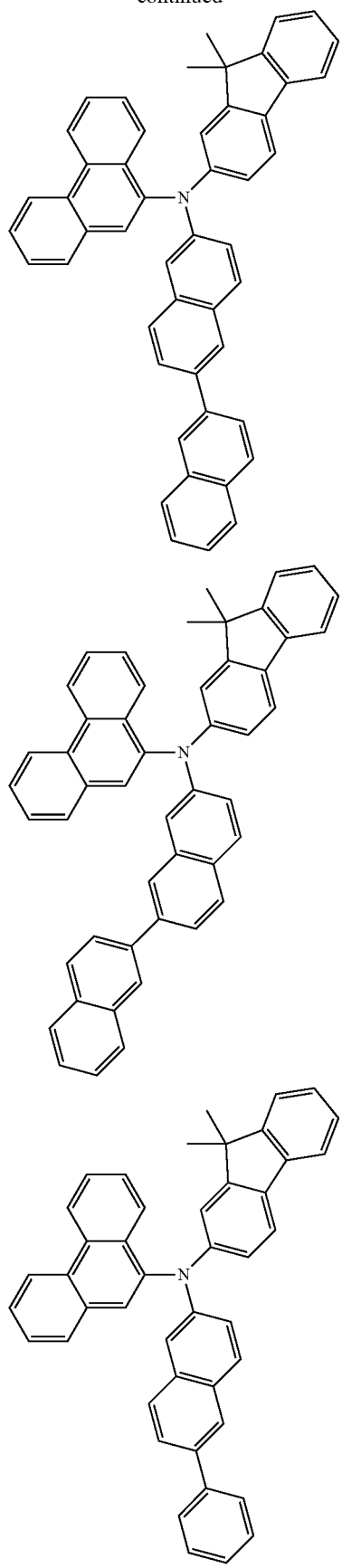
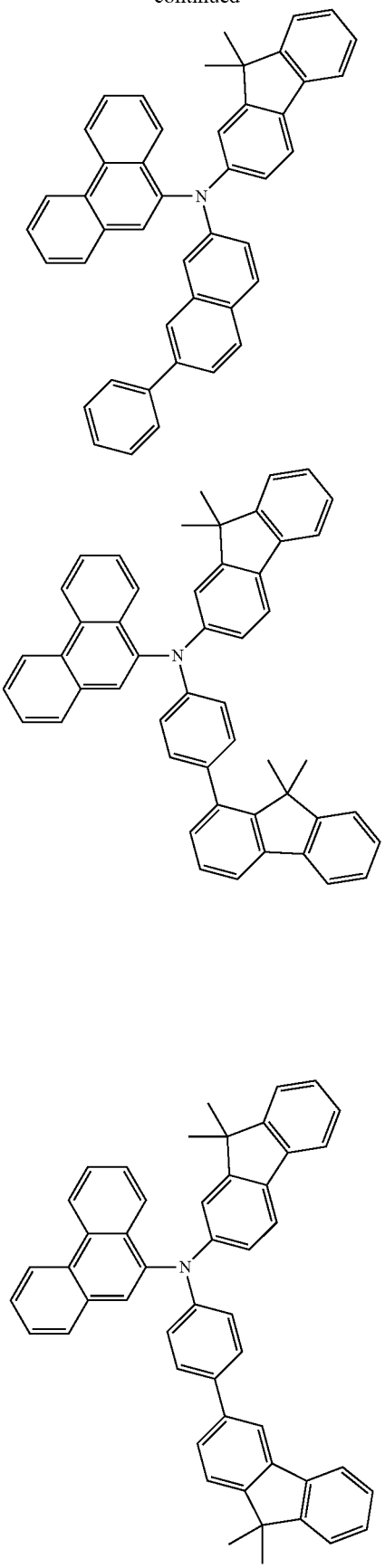

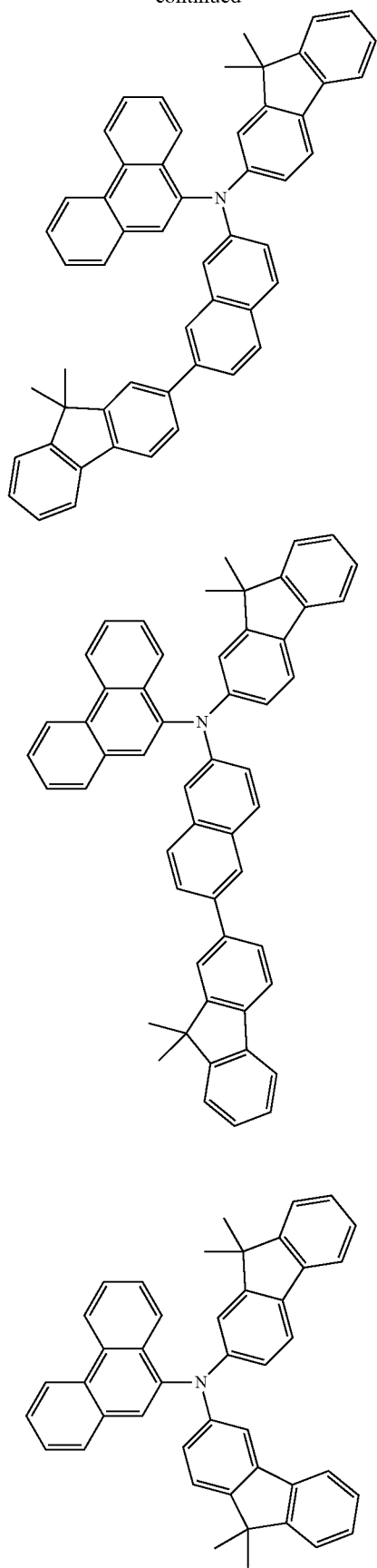
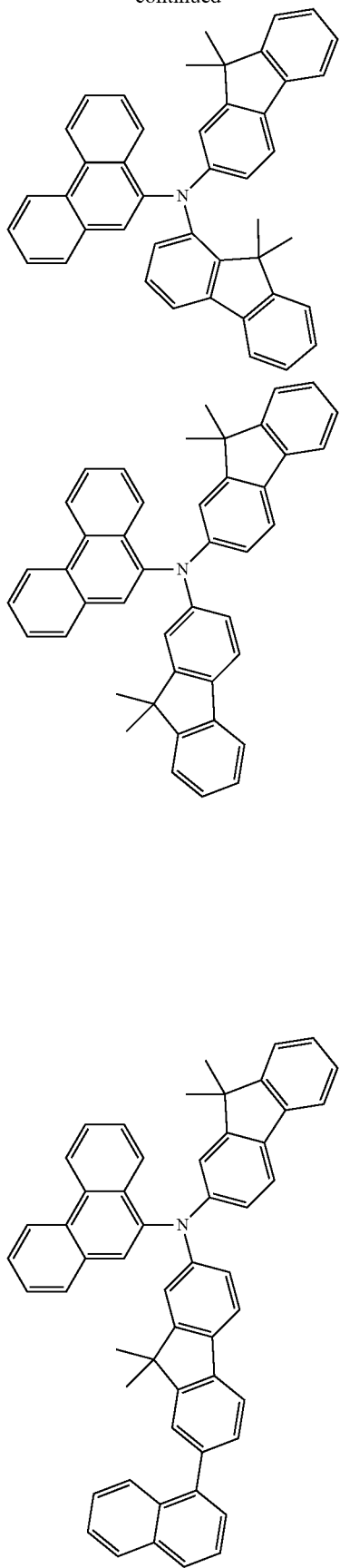

21
-continued
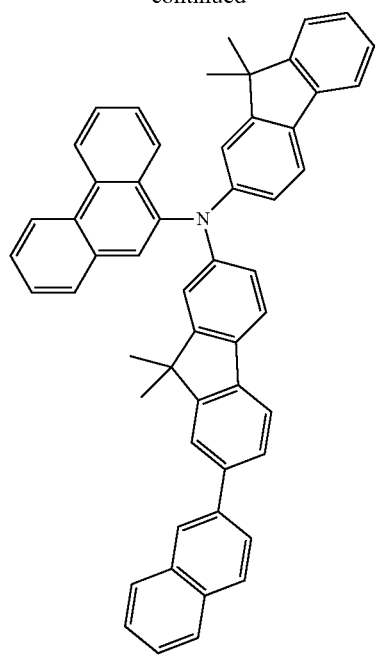
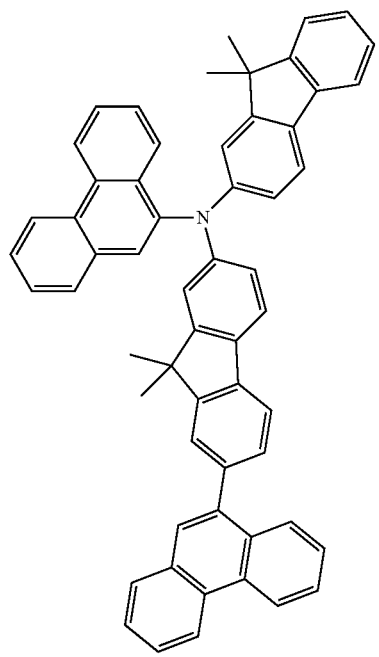
22
-continued
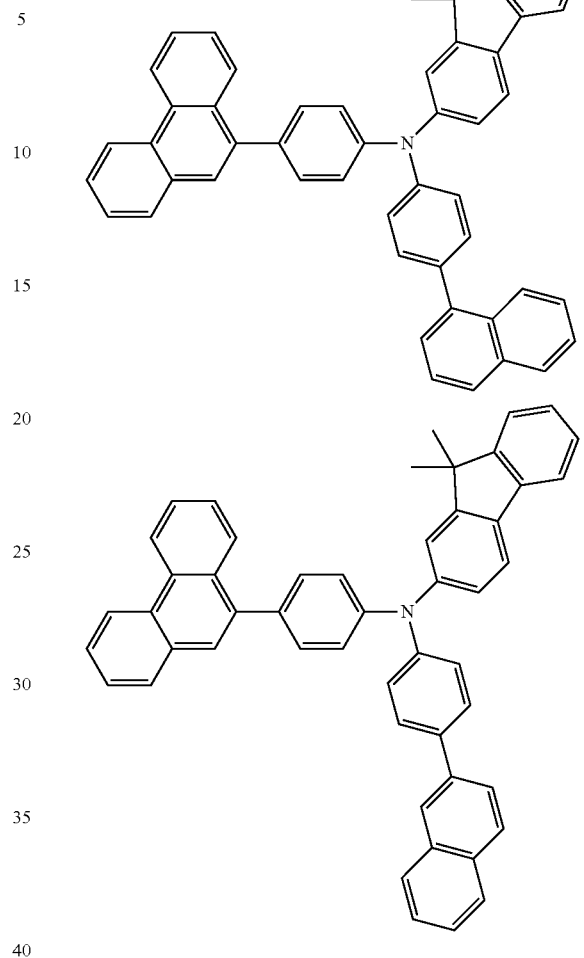
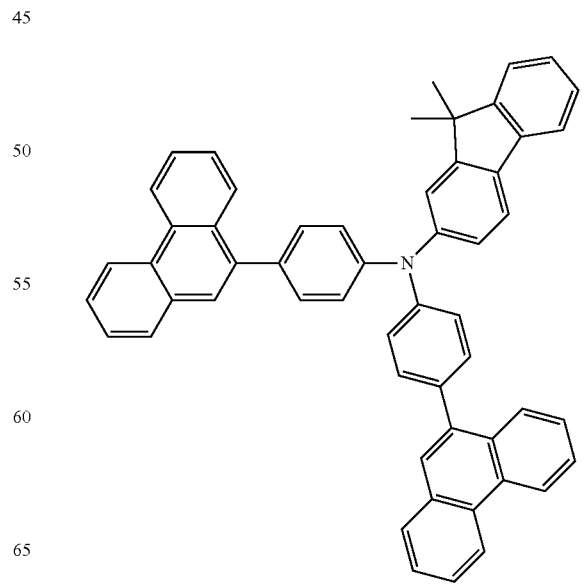

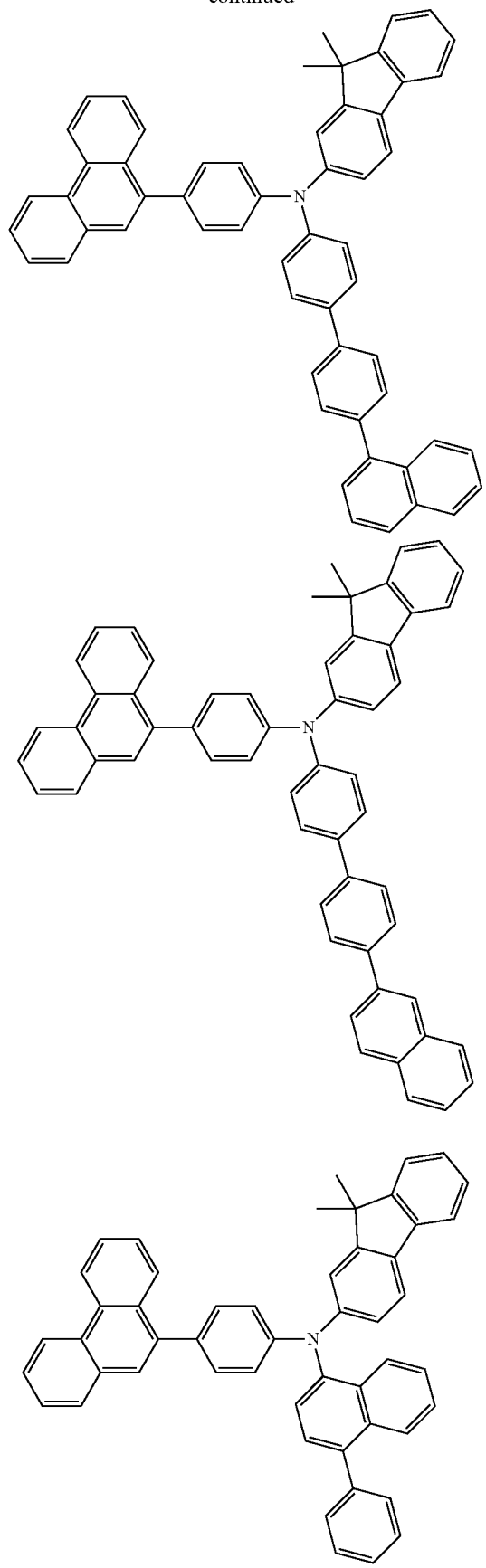
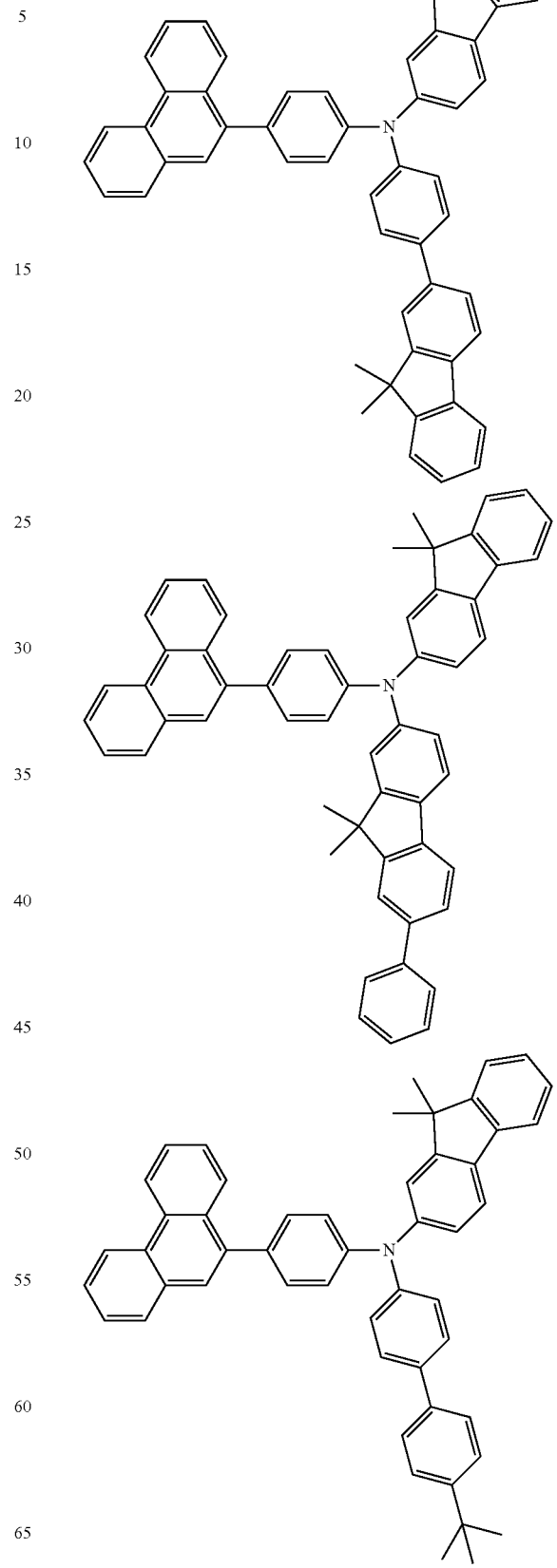

25
-continued
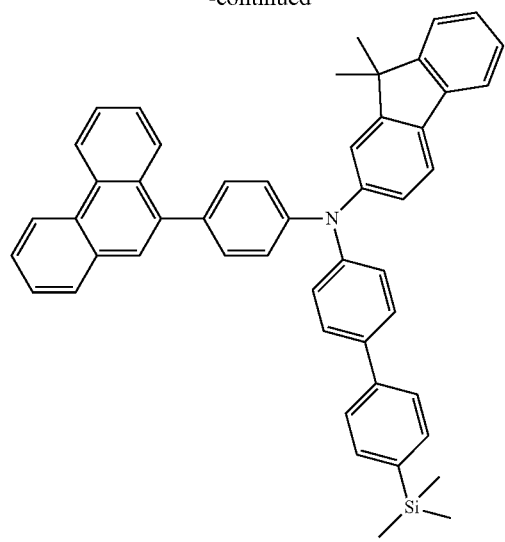
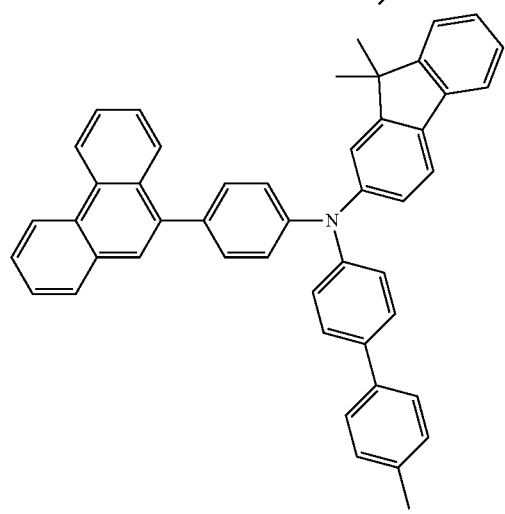
26
-continued
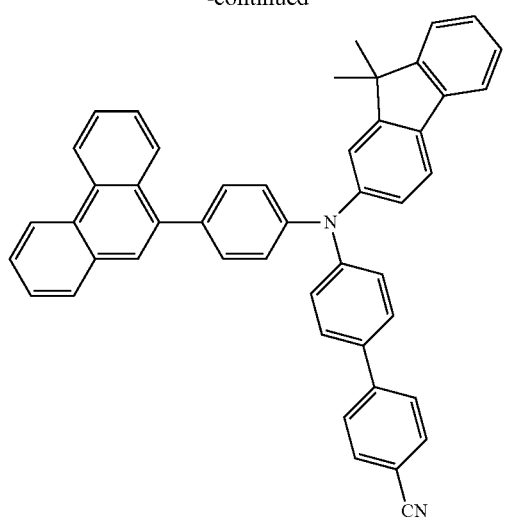
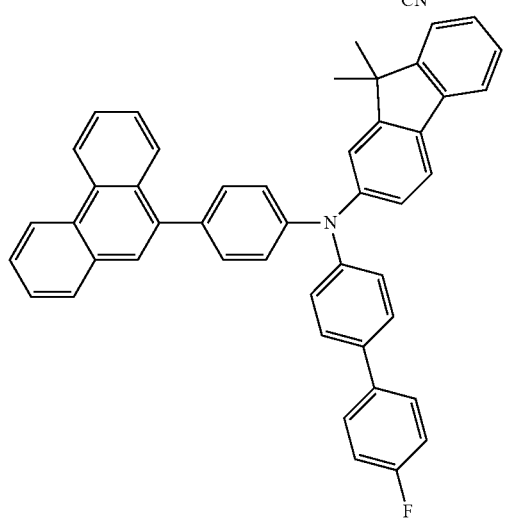
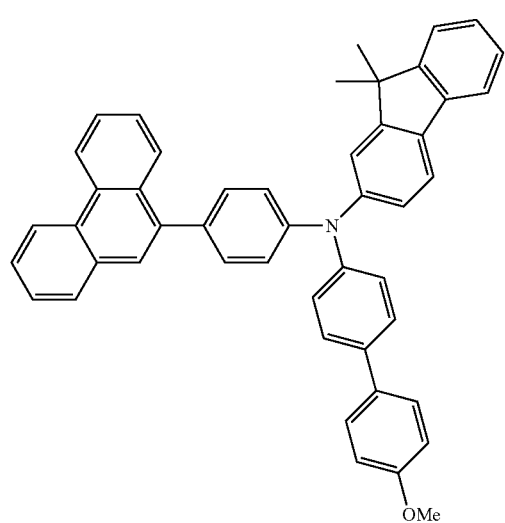
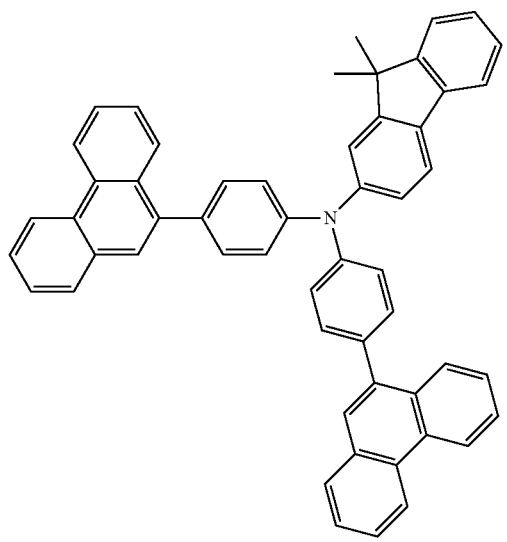

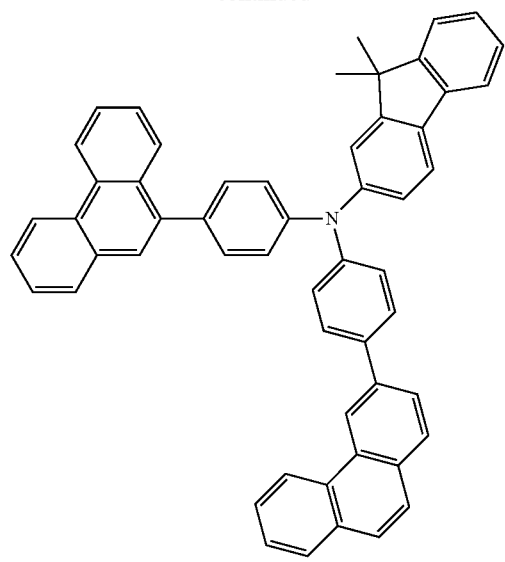
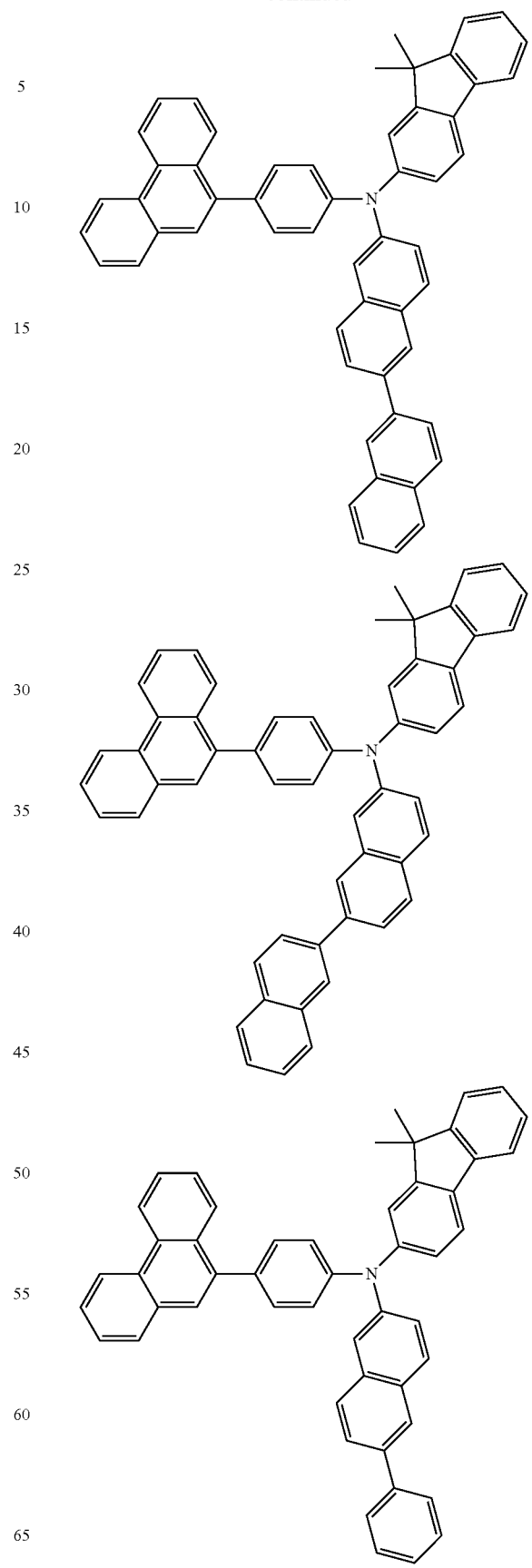

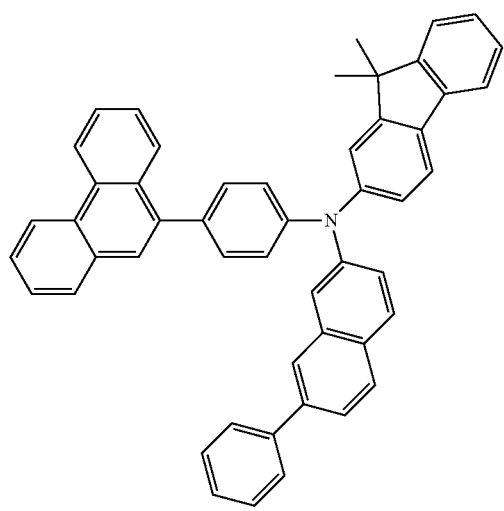 [SMILES: CC1(C)c2ccccc2-c2ccc(N(c3ccc(-c4cc5ccccc5c5ccccc45)cc3)c3ccc4ccc(-c5ccccc5)cc4c3)cc21]
According to an exemplary embodiment of the present specification, the compound of Chemical Formula 1 may be any one selected from the following structures.
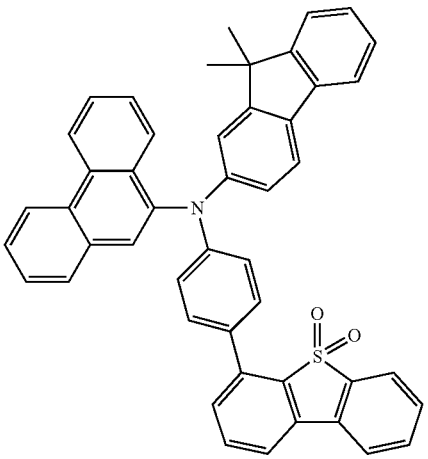
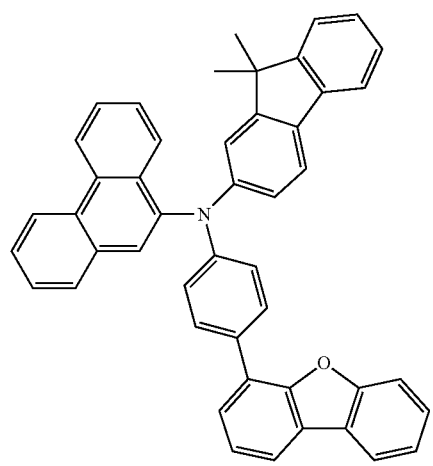
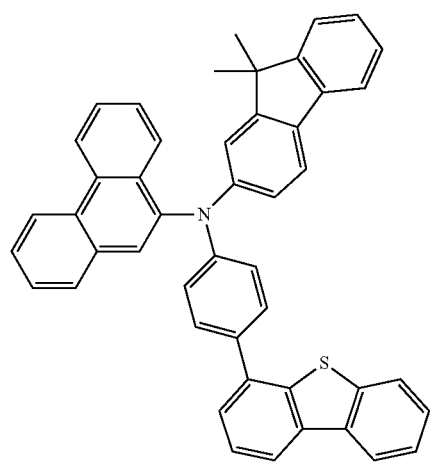
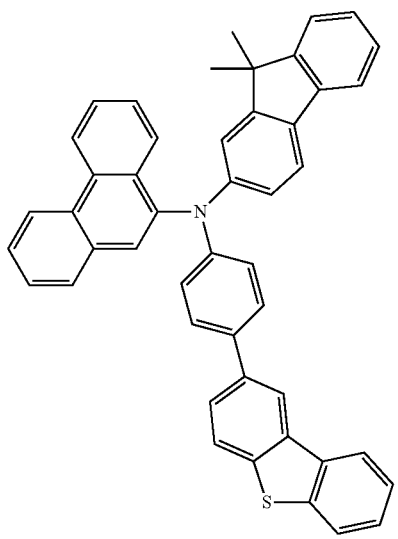

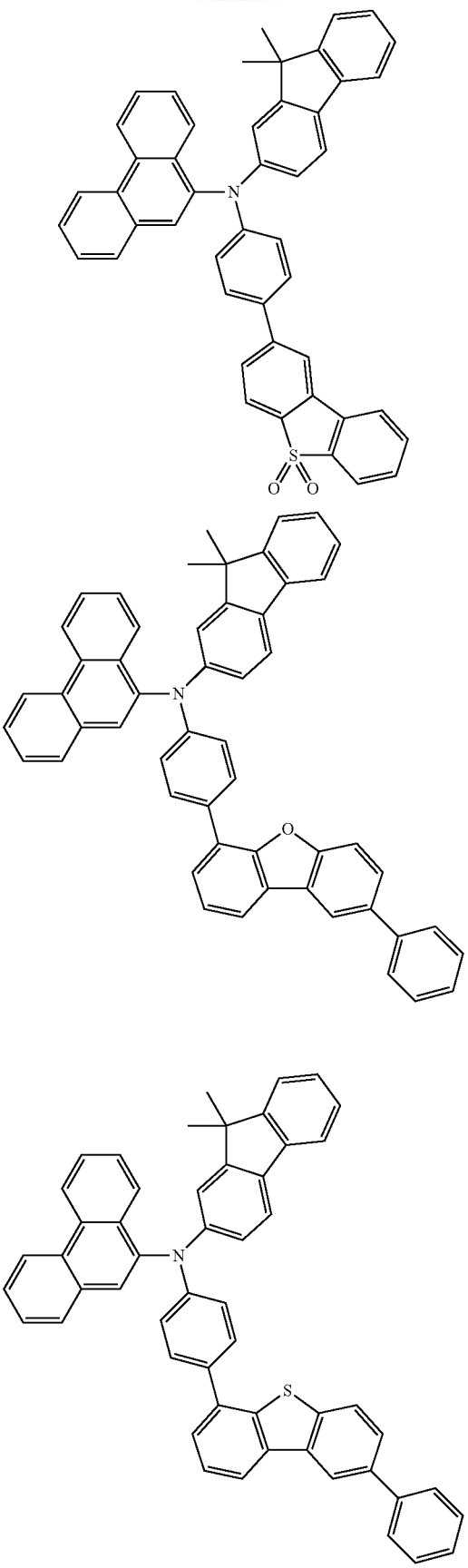
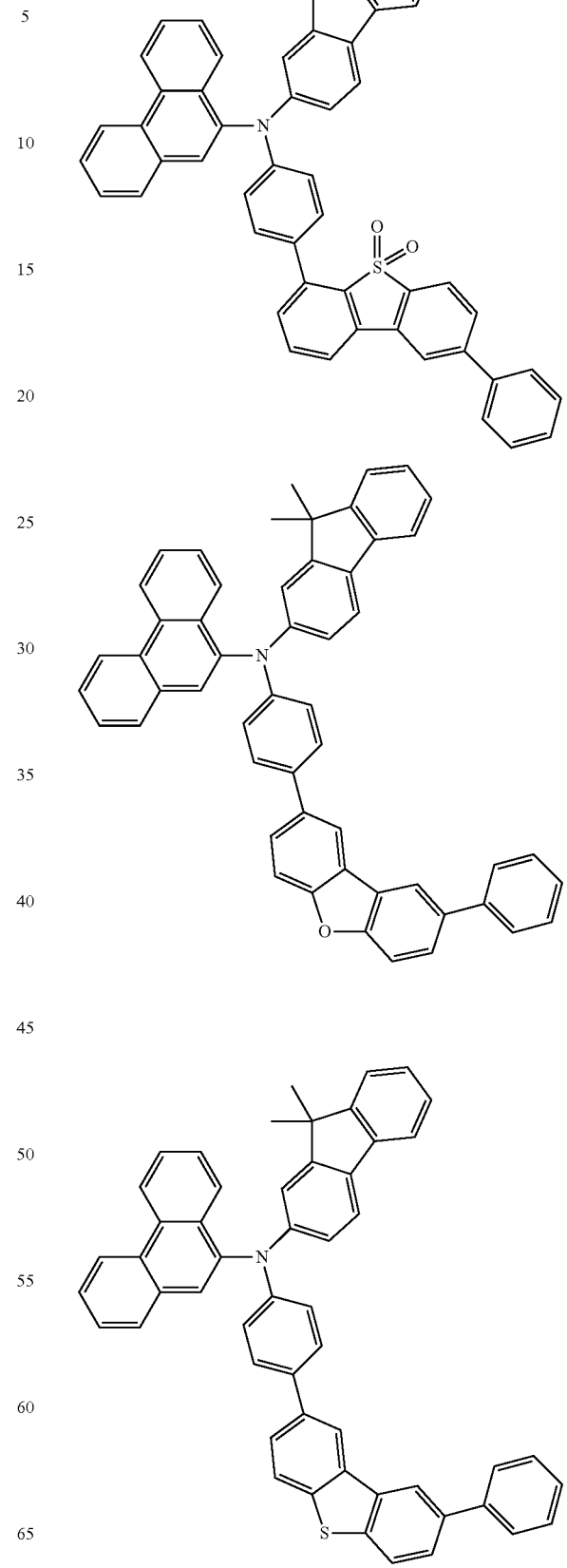

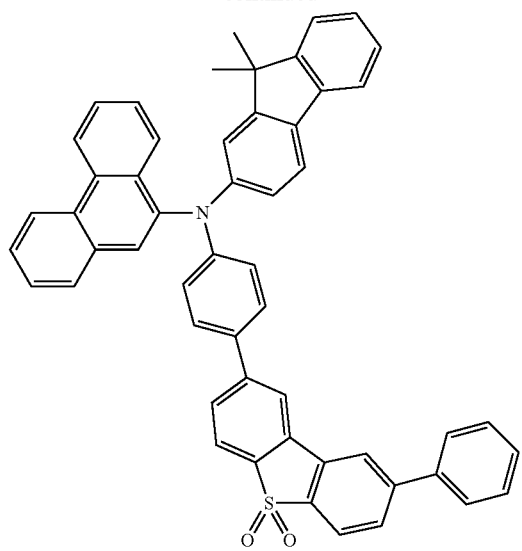
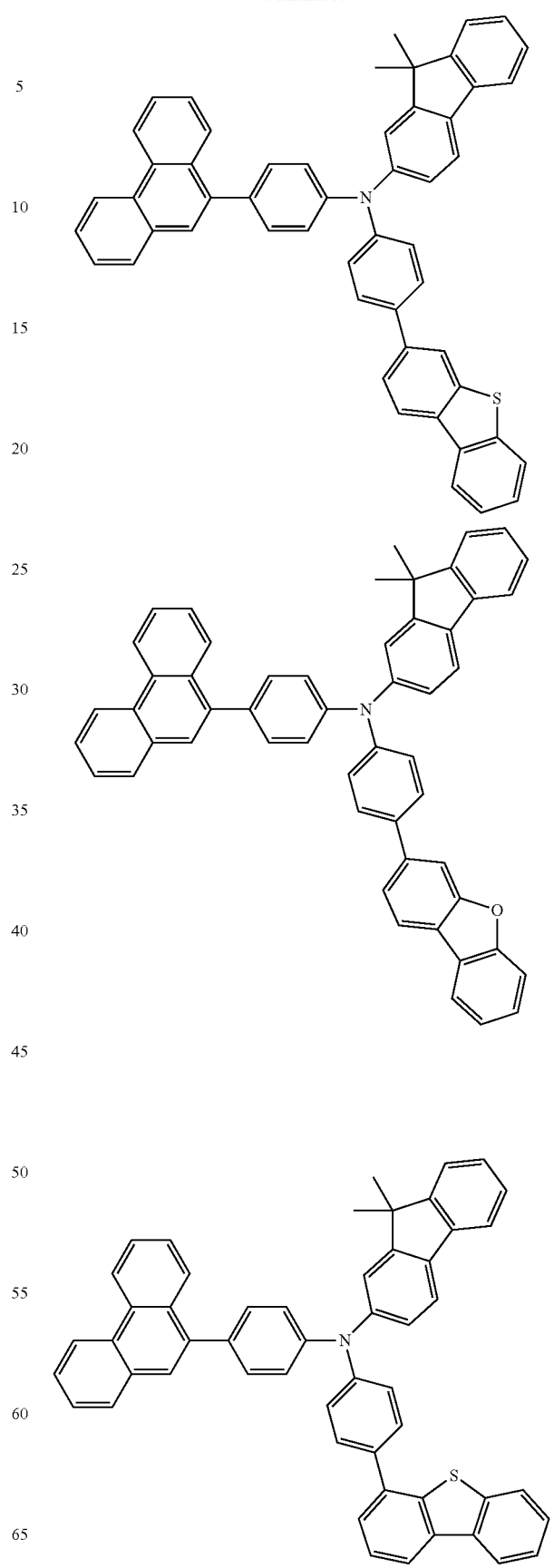

35
-continued
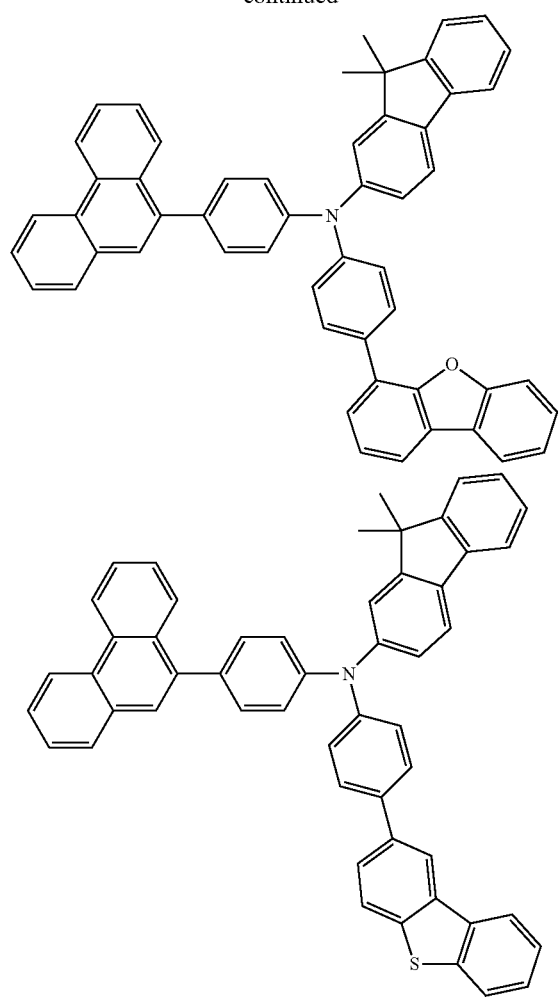
36
-continued
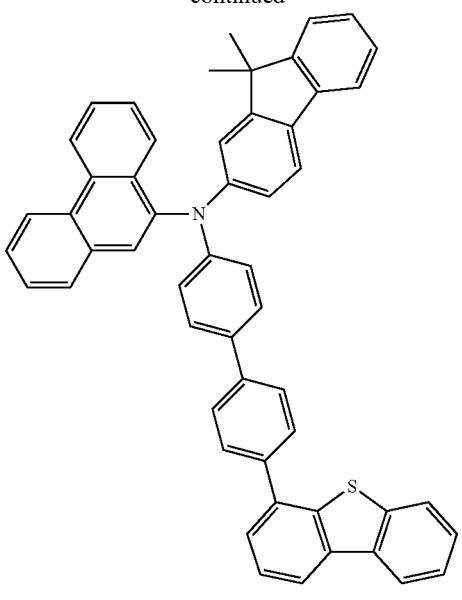
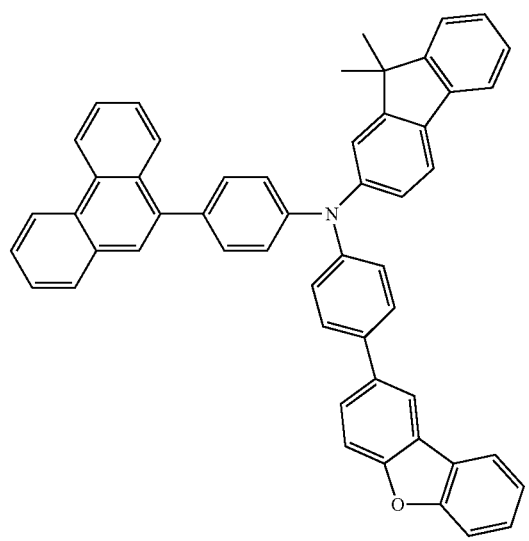
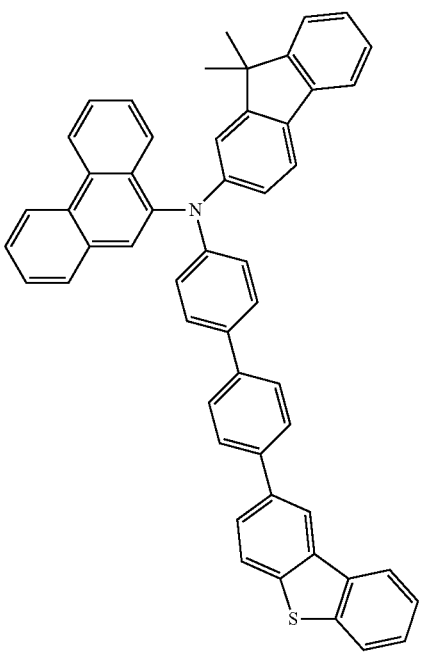

37
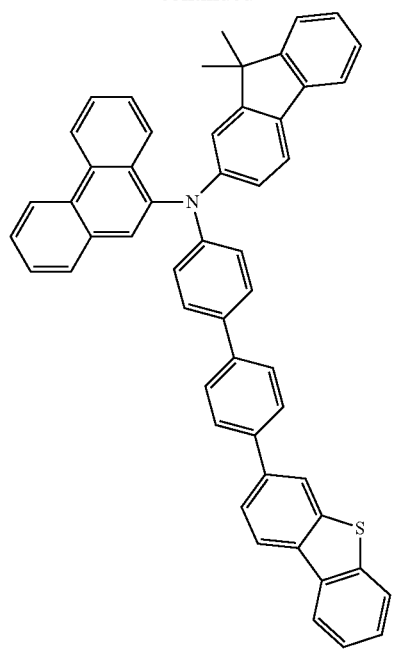
38
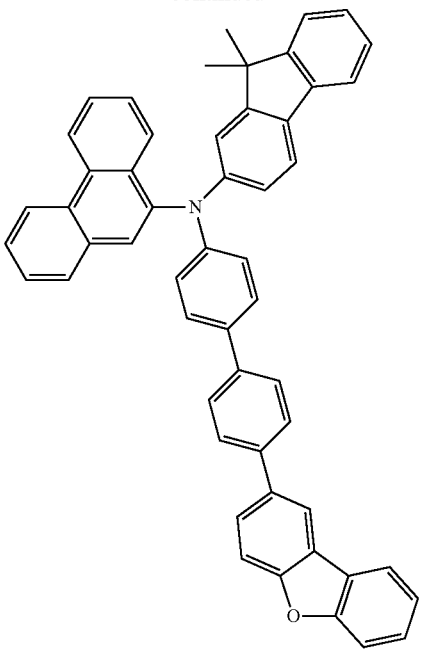
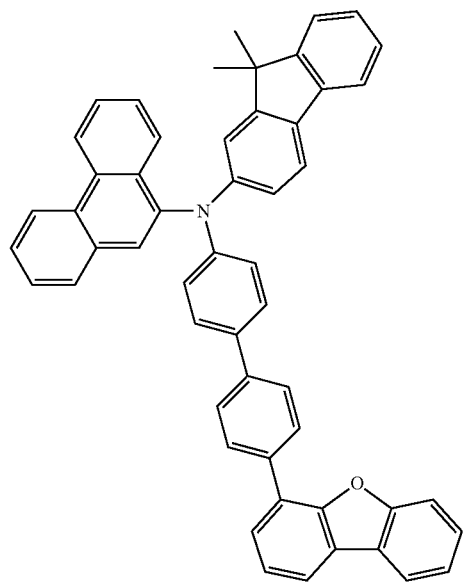
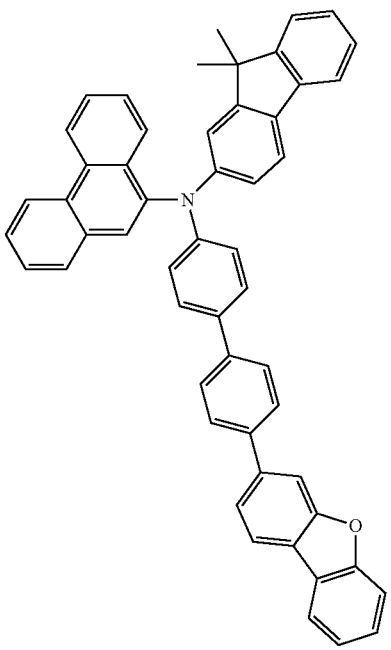

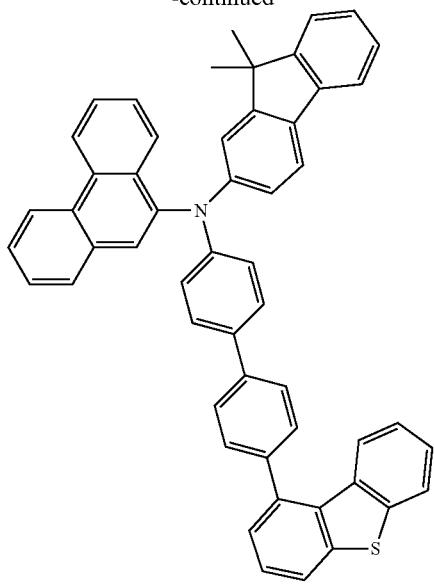

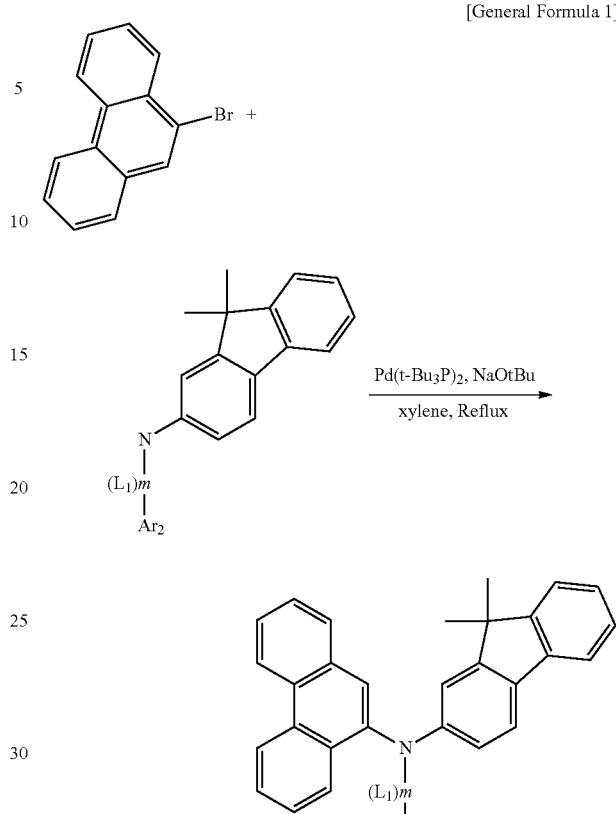

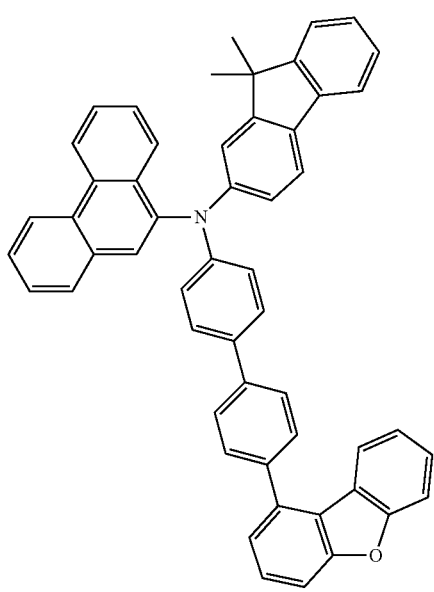

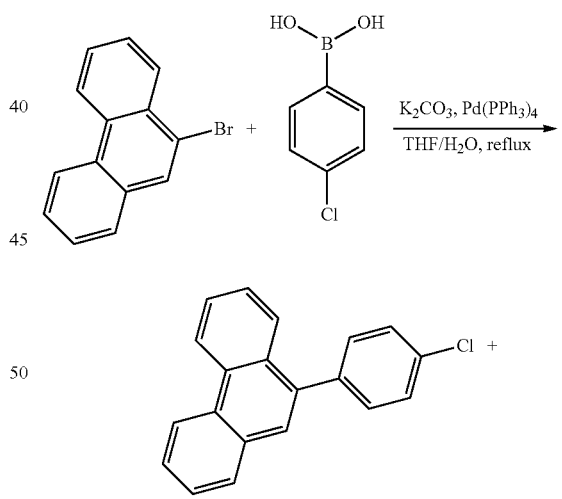

The compound according to an exemplary embodiment of the present specification may be prepared by a preparation method described below. Representative examples will be described in the Preparation Examples described below, but if necessary, a substituent may be added or excluded, and the position of the substituent may be changed. Further, a starting material, a reactant, reaction conditions, and the like may be changed based on the technology known in the art.

For example, a core structure of the compound of Chemical Formula 1 may be prepared as in the following General Formulae 1 to 4. The substituent may be bonded by a method known in the art, and the kind and position of the substituent or the number of substituents may be changed according to the technology known in the art.

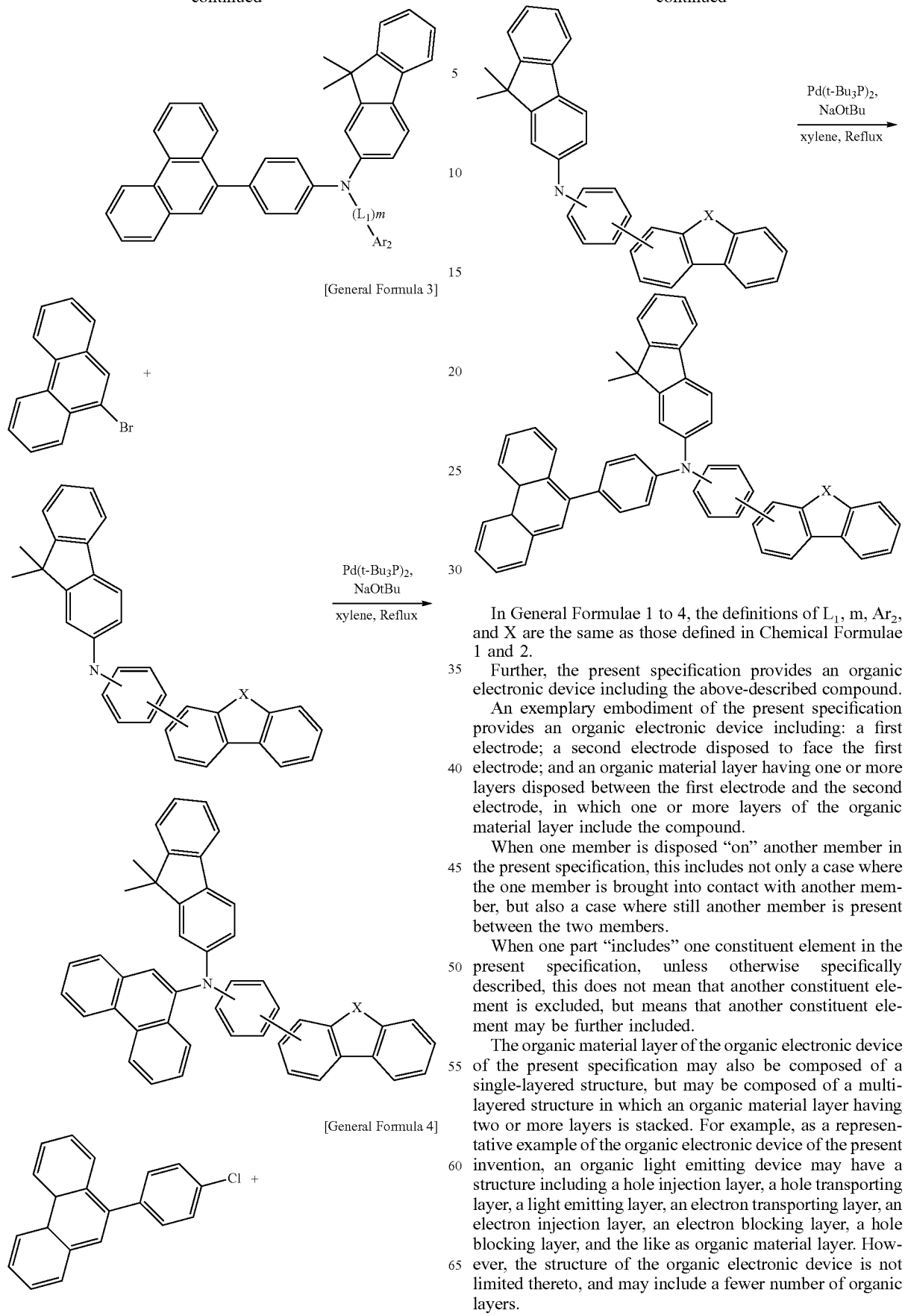

[General Formula 3]

[General Formula 4]

In General Formulae 1 to 4, the definitions of $L_1$, m, $Ar_2$, and X are the same as those defined in Chemical Formulae 1 and 2.

Further, the present specification provides an organic electronic device including the above-described compound.

An exemplary embodiment of the present specification provides an organic electronic device including: a first electrode; a second electrode disposed to face the first electrode; and an organic material layer having one or more layers disposed between the first electrode and the second electrode, in which one or more layers of the organic material layer include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic electronic device of the present specification may also be composed of a single-layered structure, but may be composed of a multi-layered structure in which an organic material layer having two or more layers is stacked. For example, as a representative example of the organic electronic device of the present invention, an organic light emitting device may have a structure including a hole injection layer, a hole transporting layer, a light emitting layer, an electron transporting layer, an electron injection layer, an electron blocking layer, a hole blocking layer, and the like as organic material layer. However, the structure of the organic electronic device is not limited thereto, and may include a fewer number of organic layers.

According to an exemplary embodiment of the present specification, the organic electronic device may be selected from the group consisting of an organic light emitting device, an organic phosphorescent device, an organic solar cell, an organic photoconductor (OPC), and an organic transistor.

Hereinafter, an organic light emitting device will be exemplified.

In an exemplary embodiment of the present specification, the organic material layer includes a light emitting layer, and the light emitting layer includes the compound.

In an exemplary embodiment of the present specification, the organic material layer includes a hole injection layer or a hole transporting layer, and the hole injection layer or the hole transporting layer includes the compound.

In an exemplary embodiment of the present specification, the organic material layer includes an electron transporting layer or an electron injection layer, and the electron transporting layer or the electron injection layer includes the compound.

In an exemplary embodiment of the present specification, the organic material layer includes an electron blocking layer or a hole blocking layer, and the electron blocking layer or the hole blocking layer includes the compound.

In an exemplary embodiment of the present specification, the organic light emitting device further includes one or two or more layers selected from the group consisting of a hole injection layer, a hole transporting layer, a light emitting layer, an electron transporting layer, an electron injection layer, a hole blocking layer, and an electron blocking layer.

In an exemplary embodiment of the present specification, the organic light emitting device includes: a first electrode; a second electrode disposed to face the first electrode; a light emitting layer disposed between the first electrode and the second electrode; and an organic material layer having two or more layers disposed between the light emitting layer and the first electrode, or between the light emitting layer and the second electrode, in which at least one of the organic material layer having two or more layers includes the compound. In an exemplary embodiment of the present specification, as the organic material layer having two or more layers, two or more may be selected from the group consisting of an electron transporting layer, an electron injection layer, a layer which transports and injects electrons simultaneously, and a hole blocking layer.

In an exemplary embodiment of the present specification, the organic material layer includes an electron transporting layer having two or more layers, and at least one of the electron transporting layer having two or more layers includes the compound. Specifically, in an exemplary embodiment of the present specification, the compound may also be included in one layer of the electron transporting layer having two or more layers, and may be included in each layer of the electron transporting layer having two or more layers.

In addition, in an exemplary embodiment of the present specification, when the compound is included in each layer of the electron transporting layer having two or more layers, the other materials except for the compound may be the same as or different from each other.

In an exemplary embodiment of the present specification, the organic material layer further includes a hole injection layer or a hole transporting layer, which includes a compound including an arylamino group, a carbazolyl group, or a benzocarbazolyl group, in addition to the organic material layer including the compound.

In another exemplary embodiment, the organic light emitting device may be an organic light emitting device having a structure (normal type) in which a positive electrode, an organic material layer having one or more layers, and a negative electrode are sequentially stacked on a substrate.

When the organic material layer including the compound of Chemical Formula 1 is an electron transporting layer, the electron transporting layer may further include an n-type dopant. As the n-type dopant, those known in the art may be used, and for example, a metal or a metal complex may be used. According to an example, the electron transporting layer including the compound of Chemical Formula 1 may further include LiQ.

In still another exemplary embodiment, the organic light emitting device may be an organic light emitting device having a reverse-direction structure (inverted type) in which a negative electrode, an organic material layer having one or more layers, and a positive electrode are sequentially stacked on a substrate.

In an exemplary embodiment of the present specification, the organic material layer includes a light emitting layer, and the light emitting layer includes a compound represented by the following Chemical Formula A-1.

[Chemical Formula A-1]

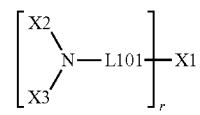

In Chemical Formula A-1,

X1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L101 is a direct bond; a substituted or unsubstituted arylene group; or a substituted or unsubstituted heteroarylene group, X2 and X3 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or may be bonded to each other to form a substituted or unsubstituted ring, r is an integer of 1 or more, and when r is 2 or more, substituents in the parenthesis are the same as or different from each other.

According to an exemplary embodiment of the present specification, the organic material layer includes a light emitting layer, and the light emitting layer includes the compound represented by Chemical Formula A-1 as a dopant of the light emitting layer.

In an exemplary embodiment of the present specification, L101 is a direct bond.

In an exemplary embodiment of the present specification, r is 2.

According to an exemplary embodiment of the present specification, X1 is a substituted or unsubstituted divalent pyrene group.

In another exemplary embodiment, X1 is a divalent pyrene group unsubstituted or substituted with an alkyl group.

In still another exemplary embodiment, X1 is a divalent pyrene group.

In an exemplary embodiment of the present specification, x2 and X3 are the same as or different from each other, and are each independently a substituted or unsubstituted aryl group having 6 to 30 carbon atoms; a substituted or unsubstituted alkyl group having 1 to 30 carbon atoms; or a substituted or unsubstituted heteroaryl group having 2 to 30 carbon atoms.

According to an exemplary embodiment of the present specification, X2 and X3 are the same as or different from each other, and are each independently a substituted or unsubstituted aryl group having 6 to 30 carbon atoms.

In an exemplary embodiment of the present specification, X2 and X3 are the same as or different from each other, and are each independently a aryl group having 6 to 30 carbon atoms which is unsubstituted or substituted with a germanium group.

In an exemplary embodiment of the present specification, X2 and X3 are a phenyl group unsubstituted or substituted with a trimethylgermanium group.

In an exemplary embodiment of the present specification, the organic material layer includes a light emitting layer, and the light emitting layer includes a compound represented by the following Chemical Formula A-2.

[Chemical Formula A-2]

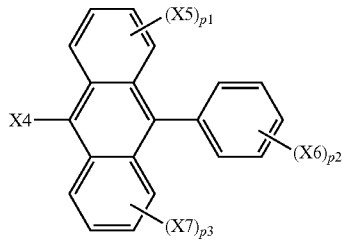

In Chemical Formula A-2,

X4 is a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

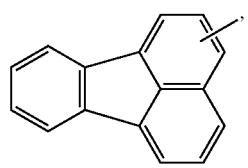

X6 is a phenyl group, a 1-naphtyl group, a 2-naphtyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthracenyl group, a 4'-methylbiphenylyl group, a 4''-t-butyl-p-terphenyl-4-yl group, or a 3-fluoranthenyl group, X5 and X7 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, p2 is an integer from 1 to 5, p1 and p3 are each an integer from 1 to 4, and when p1 to p3 are each 2 or more, substituents in the parenthesis are the same as or different from each other.

According to an exemplary embodiment of the present specification, the organic material layer includes a light emitting layer, and the light emitting layer includes the compound represented by Chemical Formula A-2 as a host of the light emitting layer.

In an exemplary embodiment of the present specification, X4 is a 1-naphthyl group, a 2-naphthyl group, a 1-anthracenyl group, a 2-anthracenyl group, a 1-phenanthryl group, a 2-phenanthryl group, a 4-phenanthryl group, a 1-naphthacenyl group, or a 1-pyrenyl group. In an exemplary embodiment of the present specification, X4 is a 1-naphthyl group, a 2-naphthyl group, or a 1-anthracenyl group.

In an exemplary embodiment of the present specification, X4 is a 1-naphthyl group.

In an exemplary embodiment of the present specification, X6 is a phenyl group, a 1-naphthyl group, a 2-naphthyl group, a 1-anthracenyl group, a 2-anthracenyl group, a 1-phenanthryl group, a 2-phenanthryl group, a 4-phenanthryl group, a 1-naphthacenyl group, or a 1-pyrenyl group.

In an exemplary embodiment of the present specification, X6 is a phenyl group, a 1-naphthyl group, a 2-naphthyl group, or a 1-anthracenyl group.

According to an exemplary embodiment of the present specification, X6 is a 2-naphthyl group, and p2 is 1. In an exemplary embodiment of the present specification, X5 and X7 are hydrogen.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, an electron blocking layer 80, a light emitting layer 40, an electron transporting layer 90, an electron injection layer 100, and a second electrode 50 are sequentially stacked on a substrate 20. FIG. 2 is an exemplified structure according to exemplary embodiments of the present specification, and may further include other organic material layers.

The organic light emitting device of the present specification may be manufactured by the materials and methods known in the art, except that one or more layers of the organic material layer include the compound of the present specification, that is, the compound.

When the organic light emitting device includes a plurality of organic material layers, the organic material layers may be formed of the same material or different materials.

The organic light emitting device of the present specification may be manufactured by the materials and methods known in the art, except that one or more layers of the organic material layer include the compound, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, materials having a large work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as $ZnO:Al$ or $SnO_2:Sb$; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a small work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as $LiF/Al$ or $LiO_2/Al$; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which may improve the service life and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

A light emitting material for the light emitting layer is a material which may emit light in a visible light region by accepting and combining holes and electrons from a hole transporting layer and an electron transporting layer, respectively, and is preferably a material having high quantum efficiency for fluorescence or phosphorescence. Specific examples thereof include: 8-hydroxy-quinoline-aluminum complex ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including Alq$_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

In an exemplary embodiment of the present specification, the compound represented by Chemical Formula 1 may be included in an organic solar cell or an organic transistor in addition to the organic light emitting device.

The compound according to the present specification may act even in organic electronic devices including organic phosphorescent devices, organic solar cells, organic photoconductors, organic transistors, and the like, based on the principle similar to those applied to organic light emitting devices.

Hereinafter, the present invention will be described in detail with reference to Examples, Comparative Examples, and the like for specifically describing the present specification. However, the Examples and the Comparative Examples according to the present specification may be modified in various forms, and it is not interpreted that the scope of the present specification is limited to the Examples and the Comparative Examples described below in detail. The Examples and the Comparative Examples of the present specification are provided to more completely explain the present specification to a person with ordinary skill in the art.

EXAMPLES

Preparation Example 1

Synthesis of Compound 1-1

(1) Synthesis of Compound A

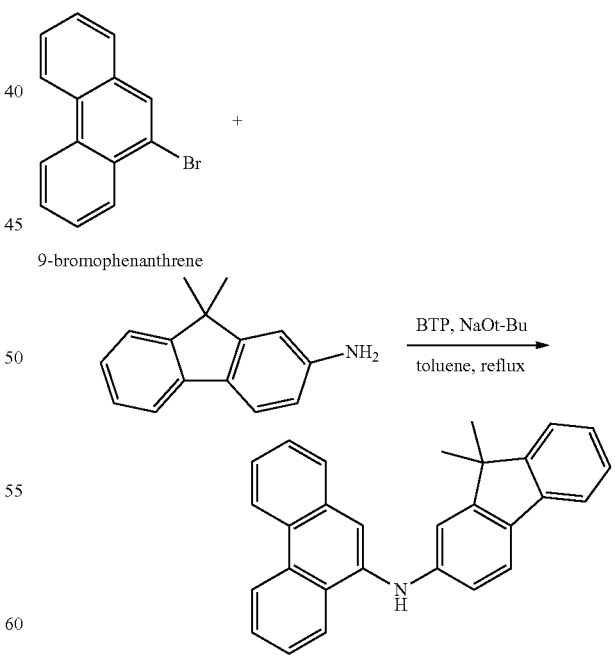

[Compound A]

Under a nitrogen atmosphere, 9-bromophenanthrene (50.0 g, 195.31 mmol) and 2-amino-9,9-dimethylfluorene (42.86 g, 205.08 mmol) were completely dissolved in 250 ml of toluene, and then sodium-tert-butoxide (22.52 g, 234.38 mmol) was added thereto, and the resulting mixture was stirred while increasing the temperature until the resulting mixture was refluxed. When the mixture began to be refluxed, bis(tri-tert-butylphosphine)palladium (0.35 g, 0.68 mmol) was slowly added dropwise thereto. After 3 hours, the reaction was terminated, the temperature was lowered to normal temperature, the resulting product was concentrated under reduced pressure, and then the residue was recrystallized with 250 ml of ethyl acetate to prepare Compound A (50.47 g, yield: 67%).

MS[M+H]$^+$=386

(2) Synthesis of Compound 1-1

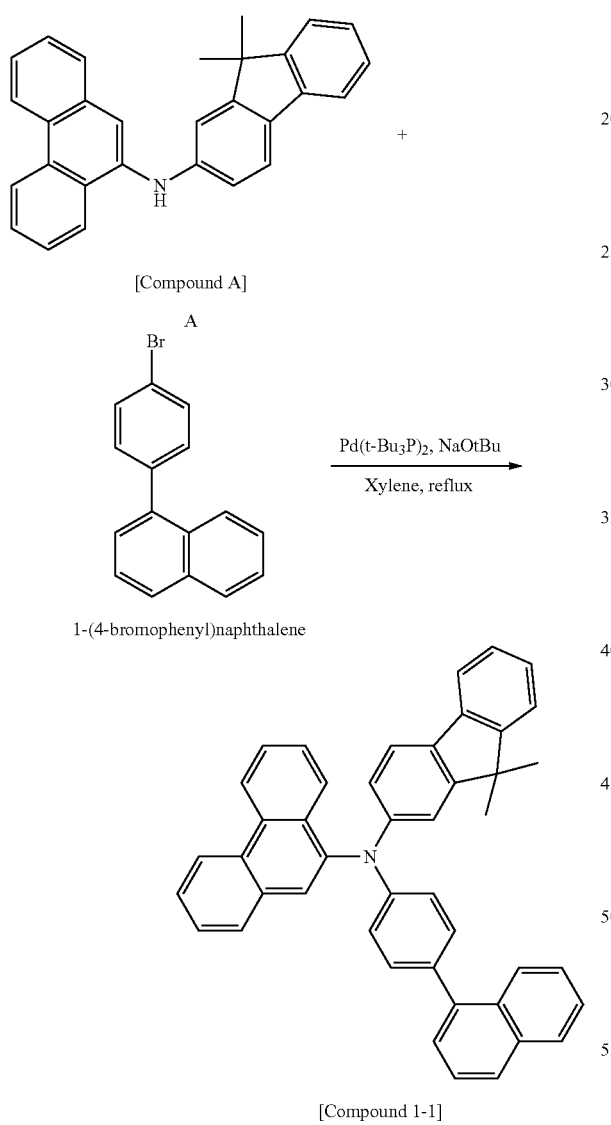

[Compound 1-1]

Under a nitrogen atmosphere, Compound A (10.0 g, 22.99 mmol) and 1-(4-bromophenyl)naphthalene (5.89 g, 20.89 mmol) were completely dissolved in 180 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 220 ml of ethyl acetate to prepare Compound 1-1 (11.52 g, yield: 79%).

MS[M+H]$^+$=638

Preparation Example 2

Synthesis of Compound 1-2

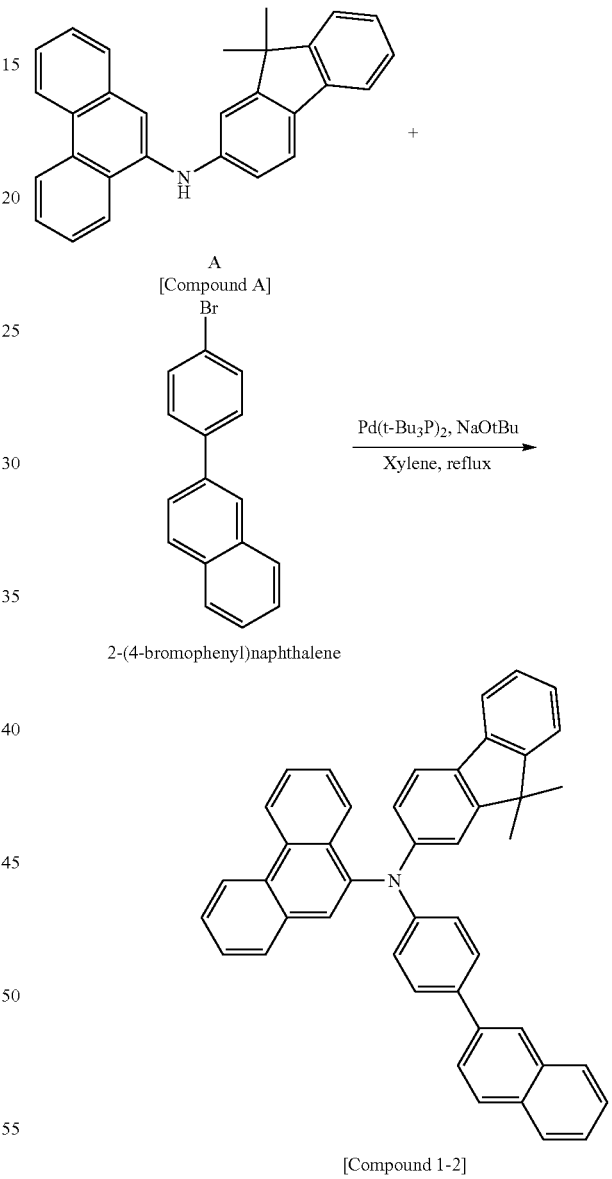

[Compound 1-2]

Under a nitrogen atmosphere, Compound A (10.0 g, 22.99 mmol) and 2-(4-bromophenyl)naphthalene (5.89 g, 20.89 mmol) were completely dissolved in 210 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 220 ml of ethyl acetate to prepare Compound 1-2 (11.52 g, yield: 79%).
MS[M+H]⁺=638

Preparation Example 3

Synthesis of Compound 1-3

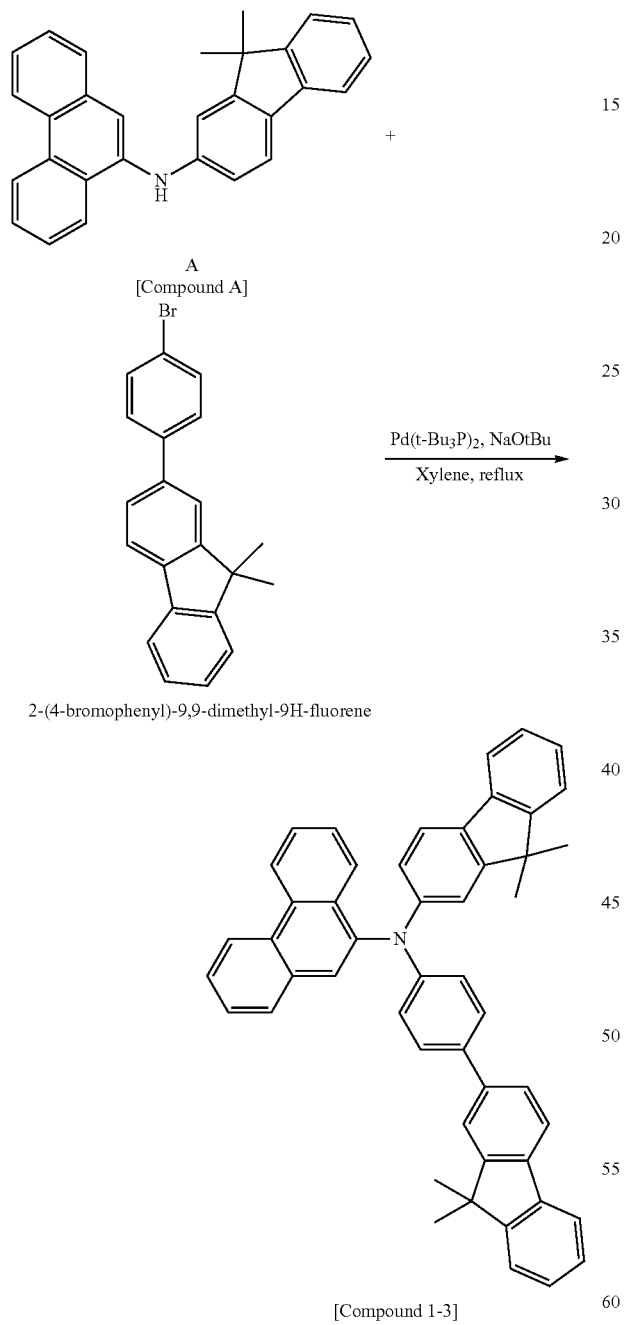

[Compound 1-3]

Under a nitrogen atmosphere, Compound A (10.0 g, 22.99 mmol) and 2-(4-bromophenyl)-9,9-dimethyl-9H-fluorene (7.27 g, 20.89 mmol) were completely dissolved in 230 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 280 ml of ethyl acetate to prepare Compound 1-3 (13.66 g, yield: 84%).
MS[M+H]⁺=704

Preparation Example 4

Synthesis of Compound 1-4

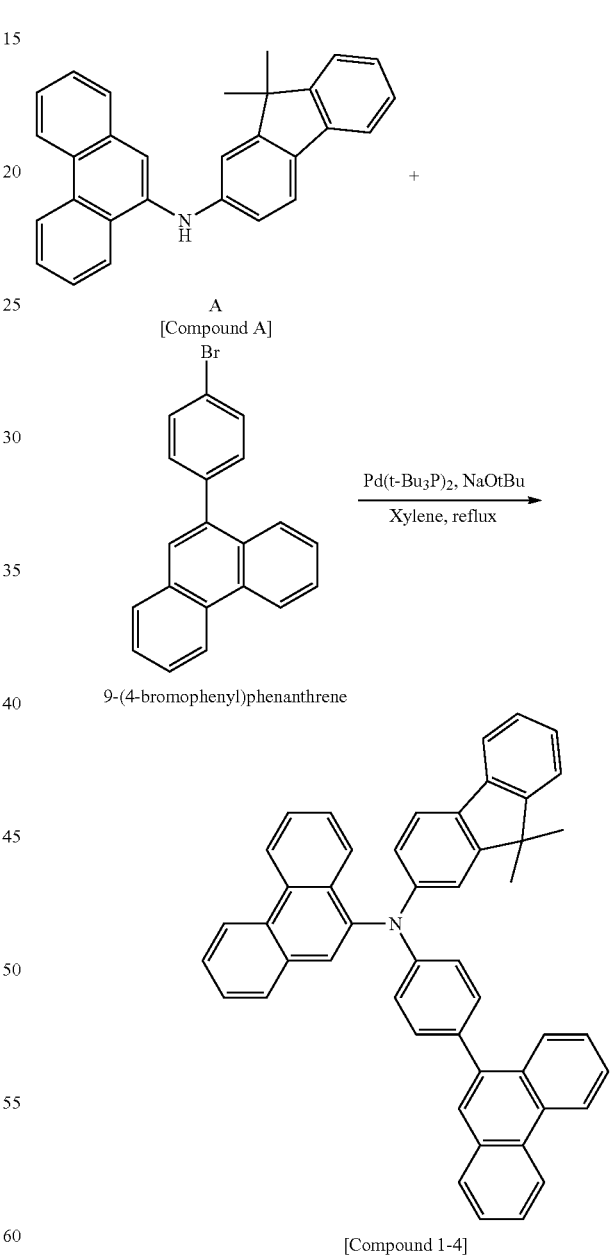

[Compound 1-4]

Under a nitrogen atmosphere, Compound A (10.0 g, 22.99 mmol) and 9-(4-bromophenyl)phenanthrene (6.94 g, 20.89 mmol) were completely dissolved in 220 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 150 ml of ethyl acetate to prepare Compound 1-4 (14.28 g, yield: 90%).
MS[M+H]$^+$=688

Preparation Example 5

Synthesis of Compound 1-5

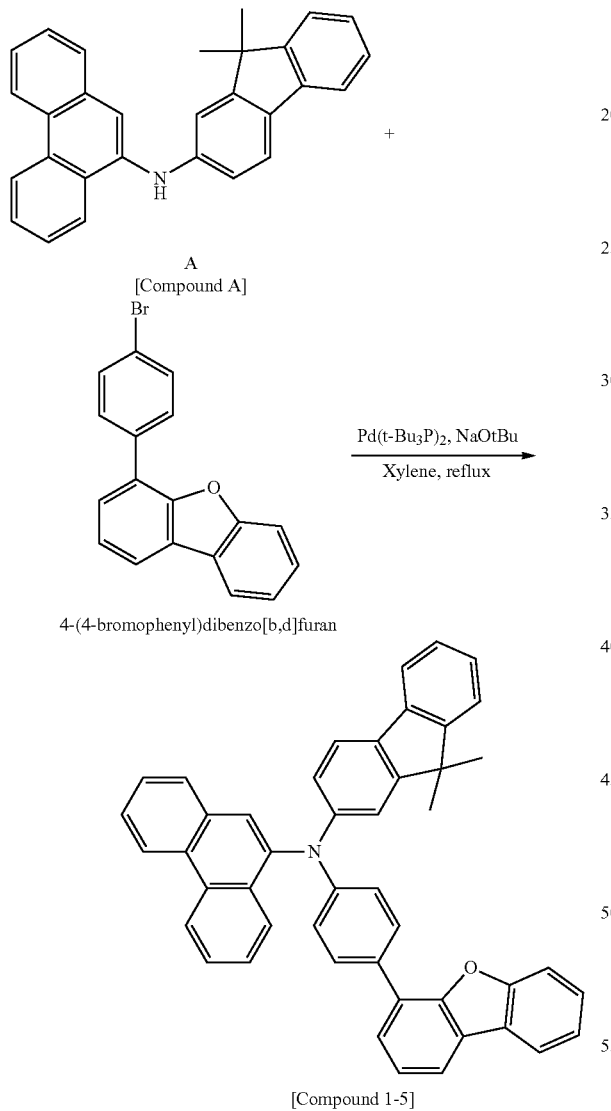

[Compound 1-5]

Under a nitrogen atmosphere, Compound A (10.0 g, 22.99 mmol) and 4-(4-bromophenyl)dibenzo[b,d]furan (6.75 g, 20.89 mmol) were completely dissolved in 260 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 280 ml of ethyl acetate to prepare Compound 1-5 (11.45 g, yield: 73%).
MS[M+H]$^+$=678

Preparation Example 6

Synthesis of Compound 1-6

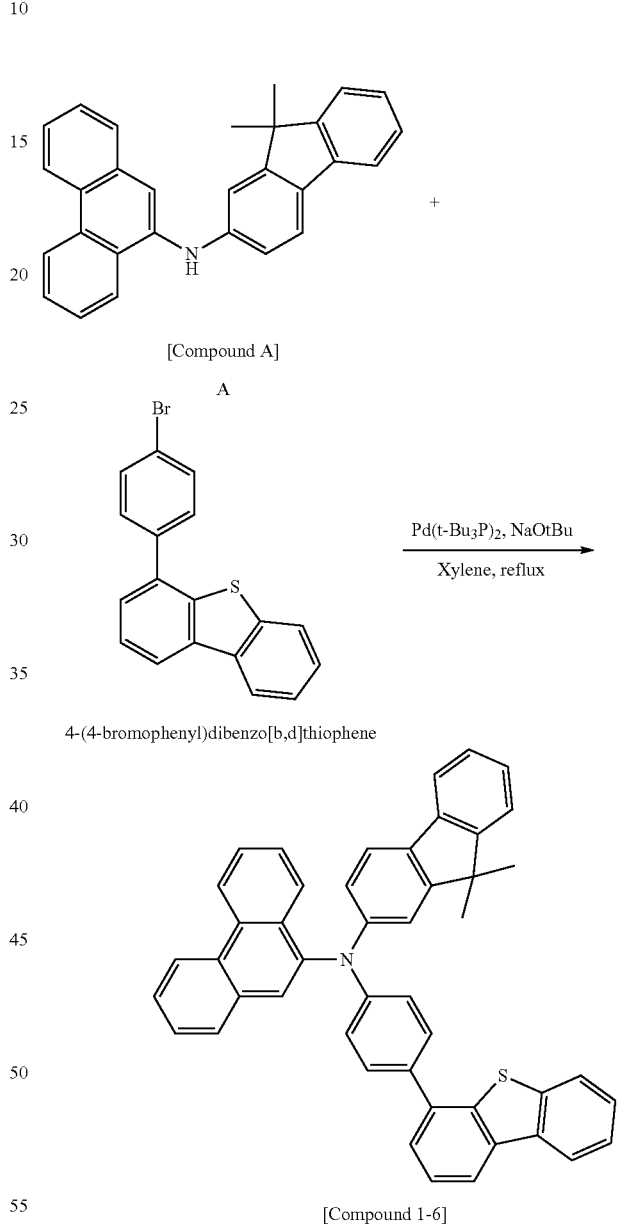

[Compound 1-6]

Under a nitrogen atmosphere, Compound A (10.0 g, 22.99 mmol) and 4-(4-bromophenyl)dibenzo[b,d]thiophene (7.06 g, 20.89 mmol) were completely dissolved in 250 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 280 ml of ethyl acetate to prepare Compound 1-6 (10.31 g, yield: 65%).
MS[M+H]$^+$=694

Preparation Example 7

Synthesis of Compound 1-7

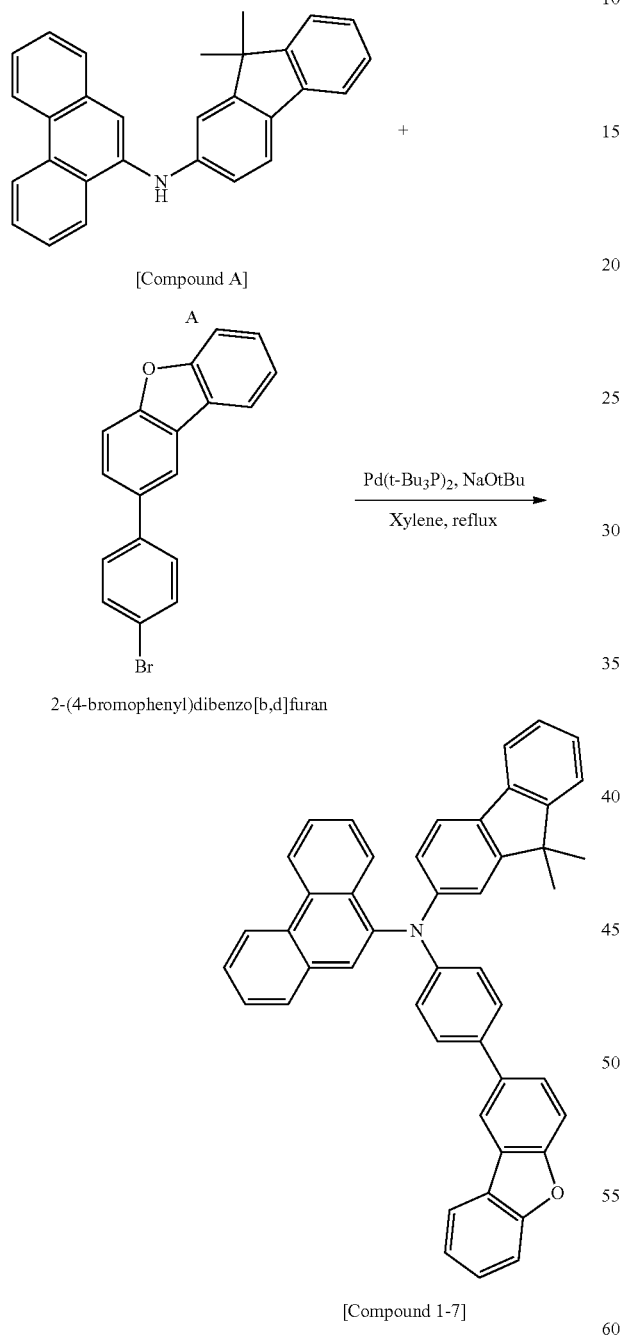

Under a nitrogen atmosphere, Compound A (10.0 g, 22.99 mmol) and 2-(4-bromophenyl)dibenzo[b,d]furan (6.73 g, 20.89 mmol) were completely dissolved in 260 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 210 ml of ethyl acetate to prepare Compound 1-7 (12.59 g, yield: 81%).
MS[M+H]$^+$=678

Preparation Example 8

Synthesis of Compound 1-8

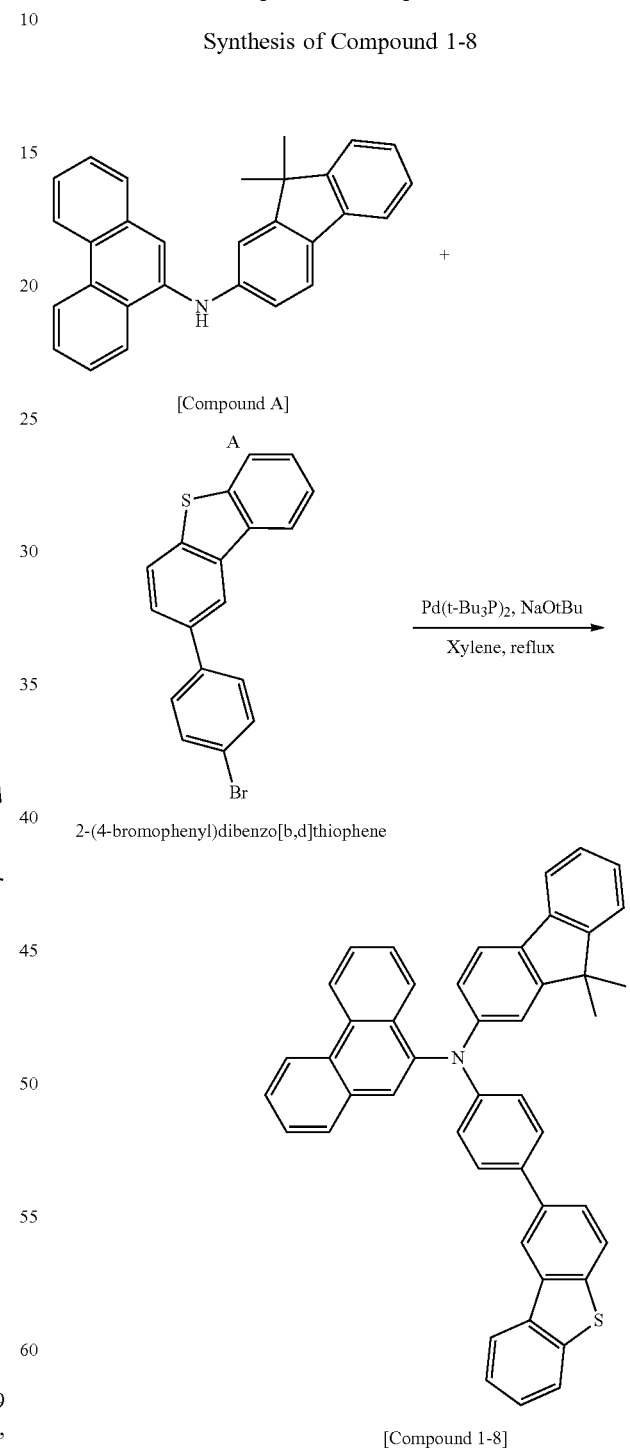

Under a nitrogen atmosphere, Compound A (10.0 g, 22.99 mmol) and 2-(4-bromophenyl)dibenzo[b,d]thiophene (7.09 g, 20.89 mmol) were completely dissolved in 250 ml of xylene in a 500-ml round bottom flask, and then sodium-tert-butoxide (2.61 g, 27.16 mol) was added thereto, bis(tri-tert-butylphosphine) palladium (0.11 g, 0.21 mmol) was put thereinto, and then the resulting mixture was heated and stirred for 4 hours. The temperature was lowered to normal temperature, the resulting mixture was filtered to remove the salt, and then xylene was concentrated under reduced pressure, and the residue was recrystallized with 280 ml of ethyl acetate to prepare Compound 1-8 (10.31 g, yield: 65%).
MS[M+H]$^{+}$=694

Preparation Example 9

Synthesis of Compound 1-9

(1) Synthesis of Compound B

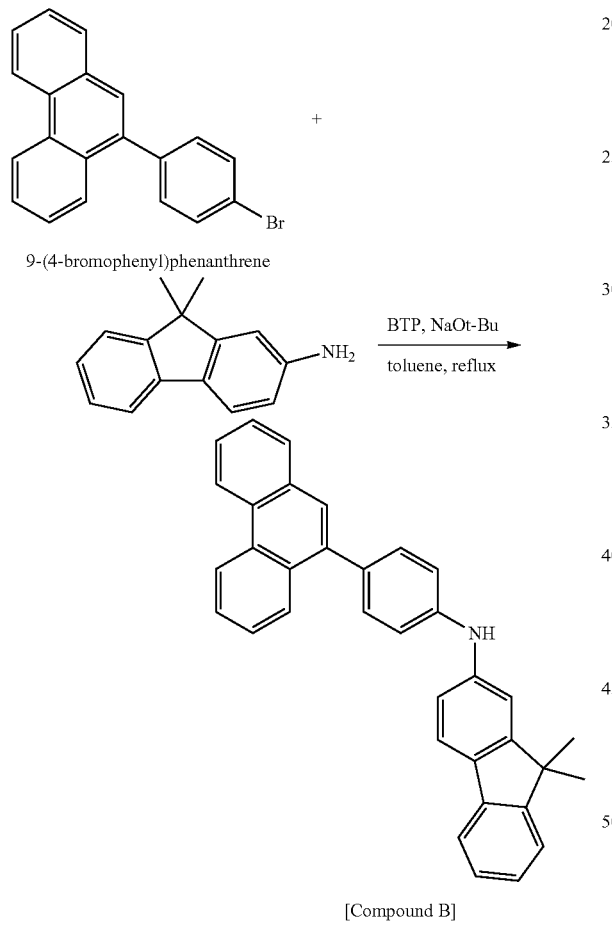

was recrystallized with 150 ml of tetrahydrofuran to prepare Compound B (19.54 g, yield: 70%).
MS[M+H]$^{+}$=462

(2) Synthesis of Compound 1-9

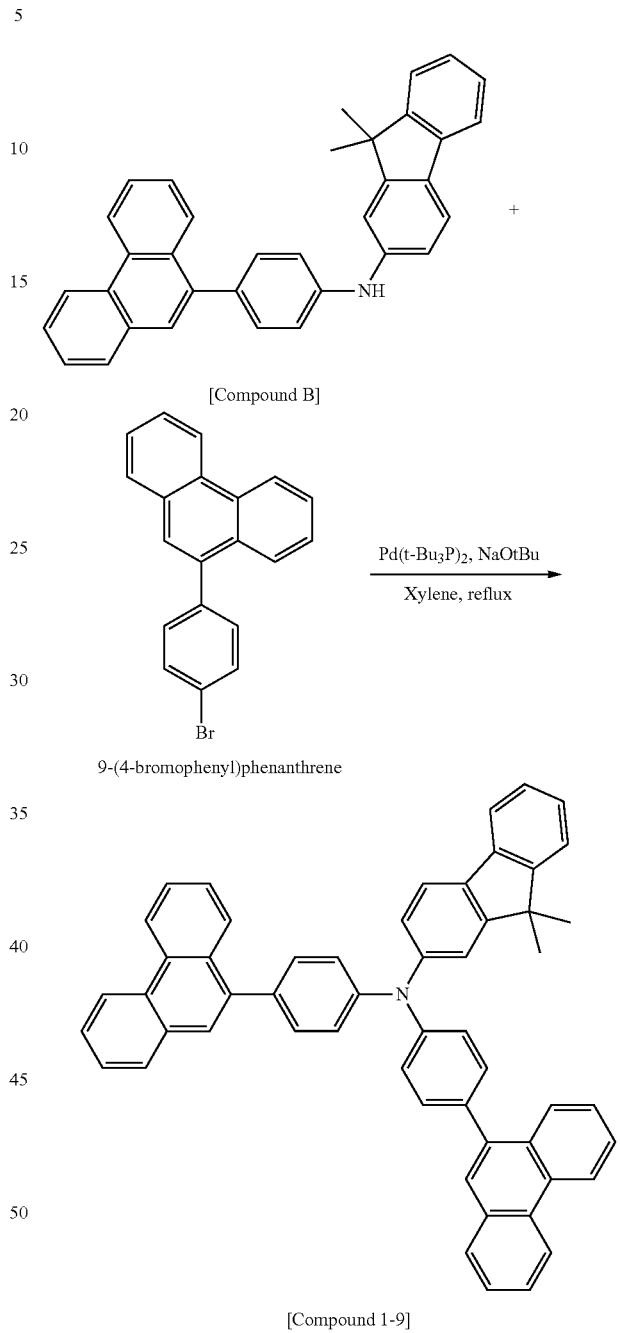

Under a nitrogen atmosphere, 9-(4-bromophenyl)phenanthrene (20.0 g, 60.24 mmol) and 2-amino-9,9-dimethylfluorene (13.22 g, 63.25 mmol) were completely dissolved in 350 ml of toluene, and then sodium-tert-butoxide (6.95 g, 72.29 mmol) was added thereto, and the resulting mixture was stirred while increasing the temperature until the resulting mixture was refluxed. When the mixture began to be refluxed, bis(tri-tert-butylphosphine)palladium (0.31 g, 0.60 mmol) was slowly added dropwise thereto. After 5 hours, the reaction was terminated, the temperature was lowered to normal temperature, the resulting product was concentrated under reduced pressure, and then the residue Under a nitrogen atmosphere, Compound B (10.0 g, 19.57 mmol) and 9-(4-bromophenyl)phenanthrene (5.91 g, 17.79 mmol) were completely dissolved in 250 ml of xylene in a 500-ml round bottom flask, and then sodium-tert-butoxide (2.22 g, 23.13 mol) was added thereto, bis(tri-tert-butylphosphine) palladium (0.09 g, 0.18 mmol) was put thereinto, and then the resulting mixture was heated and stirred for 5 hours. The temperature was lowered to normal temperature, the resulting mixture was filtered to remove the salt, and then xylene was concentrated under reduced pressure, and the residue was recrystallized with 250 ml of ethyl acetate to prepare Compound 1-9 (10.31 g, yield: 65%).
MS[M+H]$^{+}$=764

Example 1

Example 1-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

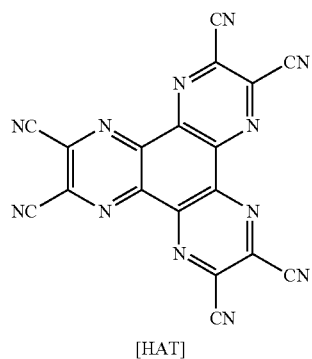

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transporting layer.

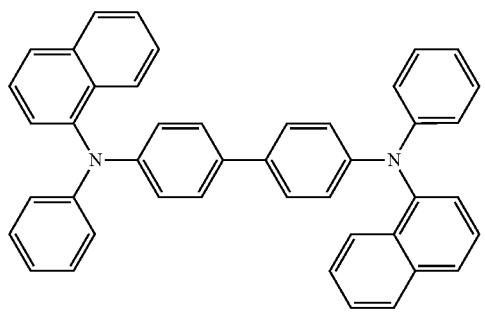

[NPB]

Subsequently, the following Compound 1-1 was vacuum deposited to have a film thickness of 100 Å on the hole transporting layer, thereby forming an electron blocking layer.

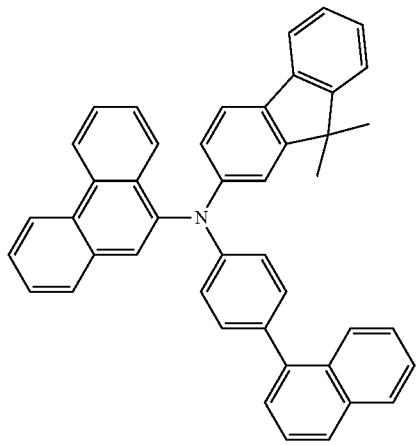

[Compound 1-1]

Subsequently, the following BH and BD were vacuum deposited at a weight ratio of 25:1 to have a film thickness of 300 Å on the electron blocking layer, thereby forming a light emitting layer.

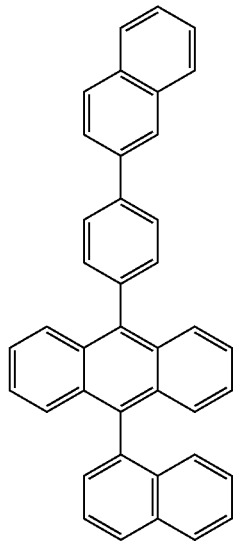

[BH]

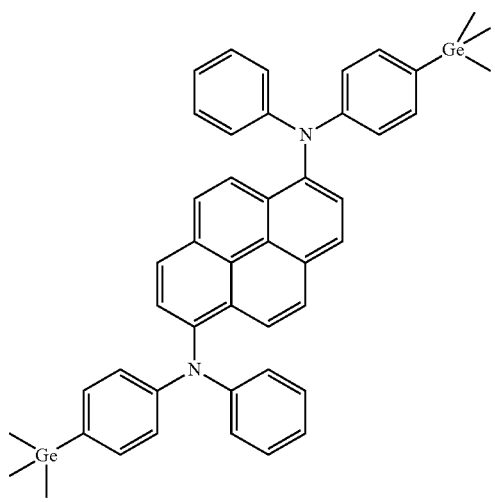

[BD]

-continued

[ET1]

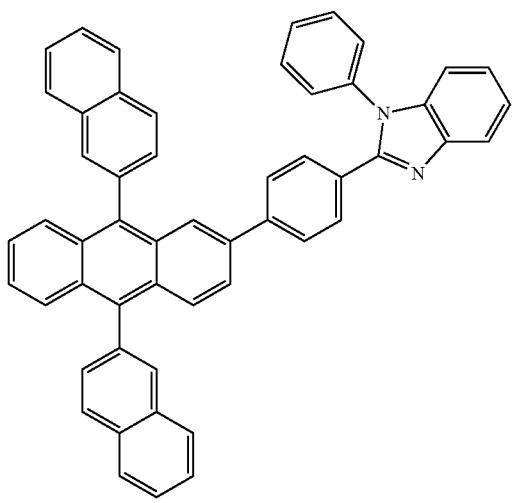

[LiQ]

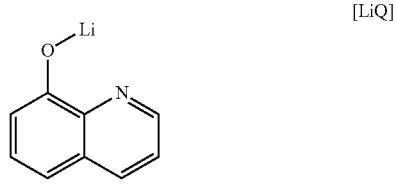

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Example 1-2

An organic light emitting device was manufactured in the same manner as in Example 1-1, except that Compound 1-2 was used instead of Compound 1-1 in Example 1-1.

Example 1-3

An organic light emitting device was manufactured in the same manner as in Example 1-1, except that Compound 1-3 was used instead of Compound 1-1 in Example 1-1.

Example 1-4

An organic light emitting device was manufactured in the same manner as in Example 1-1, except that Compound 1-4 was used instead of Compound 1-1 in Example 1-1.

Example 1-5

An organic light emitting device was manufactured in the same manner as in Example 1-1, except that Compound 1-5 was used instead of Compound 1-1 in Example 1-1.

Example 1-6

An organic light emitting device was manufactured in the same manner as in Example 1-1, except that Compound 1-6 was used instead of Compound 1-1 in Example 1-1.

Example 1-7

An organic light emitting device was manufactured in the same manner as in Example 1-1, except that Compound 1-7 was used instead of Compound 1-1 in Example 1-1.

Example 1-8

An organic light emitting device was manufactured in the same manner as in Example 1-1, except that Compound 1-8 was used instead of Compound 1-1 in Example 1-1.

Example 1-9

An organic light emitting device was manufactured in the same manner as in Example 1-1, except that Compound 1-9 was used instead of Compound 1-1 in Example 1-1.

Comparative Example 1-1

An organic light emitting device was manufactured in the same manner as in Example 1-1, except that the following EB 3 was used instead of Compound 1-1 in Example 1-1.

[EB 3]

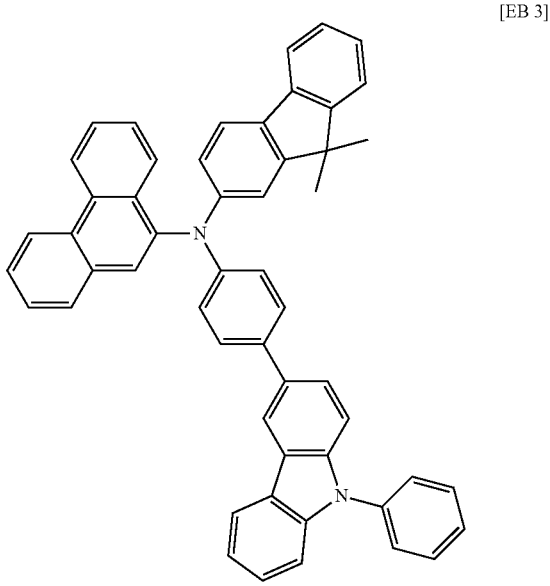 [SMILES: CC1(C)c2ccccc2-c2ccc(N(c3ccc(-c4ccc5c(c4)c4ccccc4n5-c4ccccc4)cc3)c3cc4ccccc4c4ccccc34)cc21]

Comparative Example 1-2

An organic light emitting device was manufactured in the same manner as in Example 1-1, except that the following EB 4 was used instead of Compound 1-1 in Example 1-1.

[EB 4]

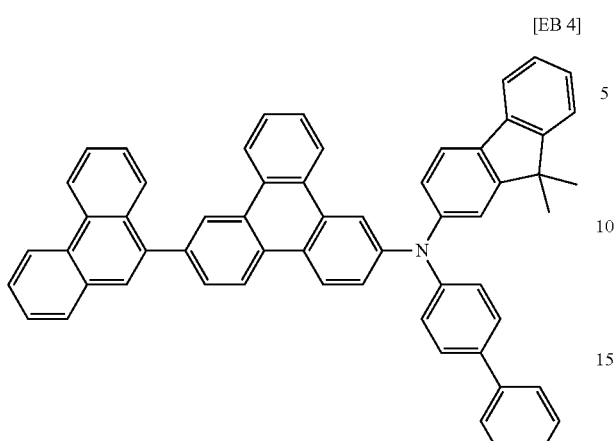

When current was applied to the organic light emitting devices manufactured in Examples 1-1 to 1-9 and Comparative Examples 1-1 and 1-2, the results of Table 1 were obtained.

TABLE 1

| Classification | Compound (Electron blocking layer) | Voltage (V@10 mA/cm$^2$) | Efficiency (cd/A@10 mA/cm$^2$) | Color coordinate (x, y) |
| --- | --- | --- | --- | --- |
| Example 1-1 | Compound 1-1 | 3.45 | 6.02 | (0.139, 0.125) |
| Example 1-2 | Compound 1-2 | 3.52 | 5.85 | (0.138, 0.126) |
| Example 1-3 | Compound 1-3 | 3.57 | 5.81 | (0.138, 0.127) |
| Example 1-4 | Compound 1-4 | 3.68 | 5.71 | (0.137, 0.125) |
| Example 1-5 | Compound 1-5 | 3.69 | 5.70 | (0.136, 0.125) |
| Example 1-6 | Compound 1-6 | 3.64 | 5.75 | (0.136, 0.127) |
| Example 1-7 | Compound 1-7 | 3.63 | 5.72 | (0.136, 0.125) |
| Example 1-8 | Compound 1-8 | 3.71 | 5.79 | (0.137, 0.125) |
| Example 1-9 | Compound 1-9 | 3.92 | 5.59 | (0.138, 0.125) |
| Comparative Example 1-1 | EB 3 | 4.32 | 5.21 | (0.139, 0.125) |
| Comparative Example 1-2 | EB 4 | 4.51 | 4.87 | (0.139, 0.127) |

As observed in Table 1, it could be seen that when the compounds in Examples 1-1 to 1-9 of the present specification were used as an electron blocking layer in an organic light emitting device, the organic light emitting devices exhibited lower voltage and higher efficiency characteristics than the organic light emitting devices in Comparative Examples 1-1 and 1-2.

Therefore, it could be confirmed that the compound derivatives of Chemical Formula 1 of the present specification had excellent electron blocking capability and thus exhibited low voltage and high efficiency characteristics, and could be applied as an electron blocking layer of an organic light emitting device.

Example 2

Examples 2-1 to 2-9

An experiment was carried out in the same manner as in Example 1, except that TCTA was used as the electron blocking layer, and the compounds in Examples 1-1 to 1-9 were used instead of NPB as the hole transporting layer.

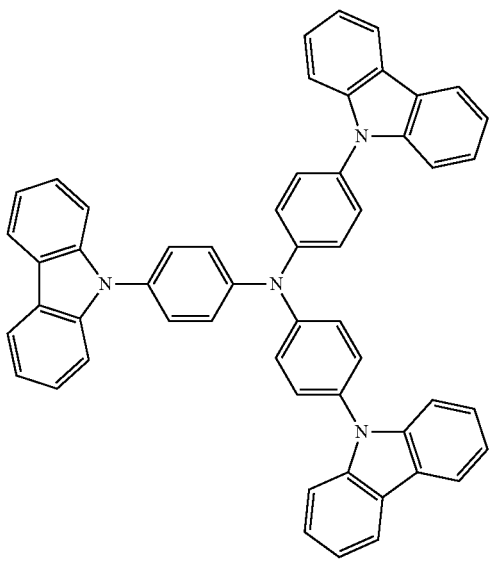

[TCTA]

Comparative Example 2-1

An experiment was carried out in the same manner as in Examples 2-1 to 2-9, except that the following HT 1 was used as the hole transporting layer.

[HT 1]

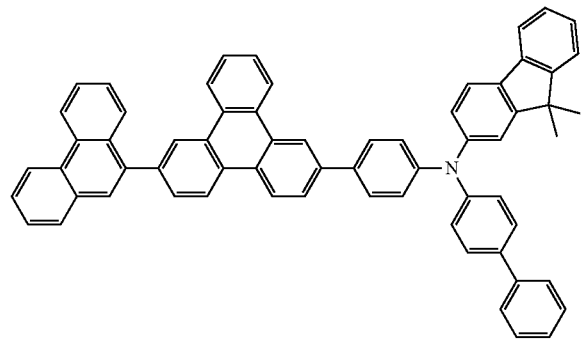

Comparative Example 2-2

An experiment was carried out in the same manner as in Examples 2-1 to 2-9, except that the following HT 3 was used as the hole transporting layer.

[HT 3]

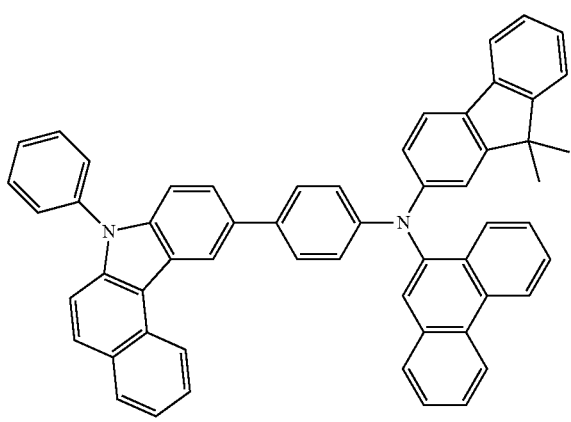

When current was applied to the organic light emitting devices manufactured in Examples 2-1 to 2-9 and Comparative Examples 2-1 and 2-2, the results of Table 2 were obtained.

TABLE 2

| Classification | Compound (Hole transporting layer) | Voltage (V@10 mA/cm$^2$) | Efficiency (cd/A@10 mA/cm$^2$) | Color coordinate (x, y) |
|---|---|---|---|---|
| Example 2-1 | Compound 1-1 | 3.75 | 5.95 | (0.139, 0.126) |
| Example 2-2 | Compound 1-2 | 3.72 | 5.98 | (0.138, 0.126) |
| Example 2-3 | Compound 1-3 | 3.87 | 5.85 | (0.138, 0.127) |
| Example 2-4 | Compound 1-4 | 3.88 | 5.84 | (0.137, 0.125) |
| Example 2-5 | Compound 1-5 | 3.89 | 5.82 | (0.136, 0.125) |
| Example 2-6 | Compound 1-6 | 3.84 | 5.83 | (0.136, 0.127) |
| Example 2-7 | Compound 1-7 | 3.83 | 5.80 | (0.136, 0.125) |
| Example 2-8 | Compound 1-8 | 3.84 | 5.81 | (0.137, 0.125) |
| Example 2-9 | Compound 1-9 | 3.93 | 5.71 | (0.138, 0.125) |
| Comparative Example 2-1 | HT 1 | 4.55 | 4.83 | (0.138, 0.127) |
| Comparative Example 2-2 | HT 3 | 4.44 | 4.94 | (0.139, 0.126) |

As observed in Table 2, it could be seen that when the compounds in Examples 2-1 to 2-9 of the present specification were used as a hole transporting layer in an organic light emitting device, the organic light emitting devices exhibited lower voltage and higher efficiency characteristics than the organic light emitting devices in Comparative Examples 2-1 and 2-2.

Therefore, it could be confirmed that the compound derivatives of Chemical Formula 1 of the present specification had excellent hole transporting capability and thus exhibited low voltage and high efficiency characteristics, and could be applied as a hole transporting layer of an organic light emitting device.

Although the preferred exemplary embodiments (an electron blocking layer and a hole transporting layer) of the present specification have been described above, the present invention is not limited thereto, and can be variously modified and carried out within the scope of the claims and the detailed description of the invention, and the modifications also fall within the scope of the specification.

EXPLANATION OF REFERENCE NUMERALS AND SYMBOLS

10, 11: Organic light emitting device
20: Substrate
30: First electrode
40: Light emitting layer
50: Second electrode
60: Hole injection layer
70: Hole transporting layer
80: Electron blocking layer
90: Electron transporting layer
100 Electron injection layer

The invention claimed is:
1. An organic electronic device comprising:
a first electrode;
a second electrode disposed to face the first electrode; and
an organic material layer having one or more layers disposed between the first electrode and the second electrode,
wherein the organic material layer comprises an electron blocking layer or a hole transporting layer, and the electron blocking layer or the hole transporting layer comprises a compound that is any one selected from the following structures:

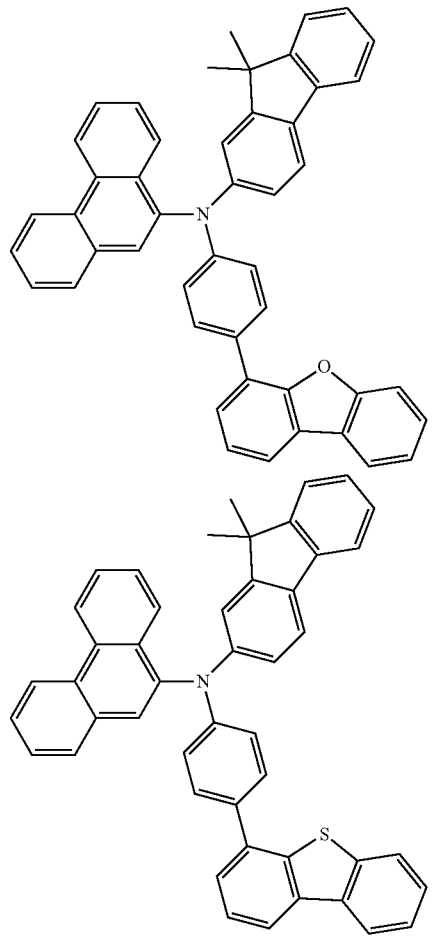

-continued

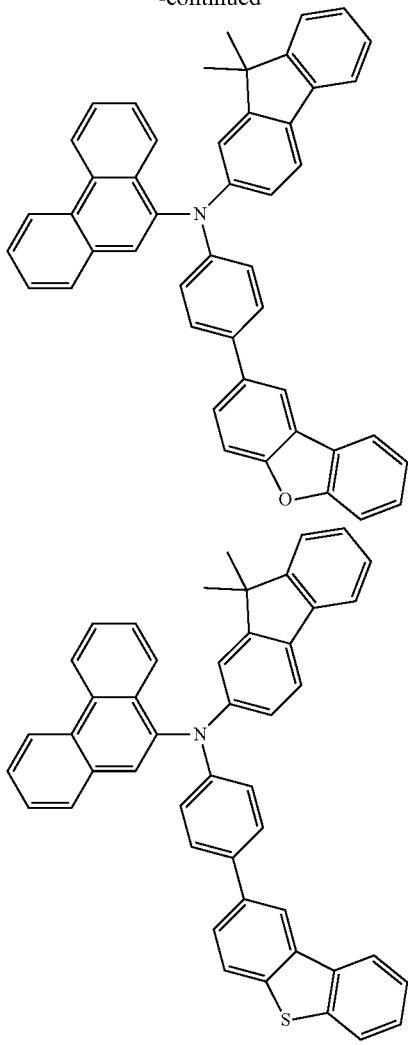

and
wherein the organic material layer comprises a light emitting layer, and the light emitting layer comprises a compound represented by the following Chemical Formula A-1:

[Chemical Formula A-1]

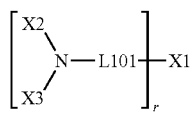

in Chemical Formula A-1,
X1 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L101 is a direct bond; a substituted or unsubstituted arylene group; or a substituted or unsubstituted heteroarylene group,
X2 and X3 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or are optionally bonded to each other to form a substituted or unsubstituted ring,
r is an integer of 1 or more, and
when r is 2 or more, substituents in the parenthesis are the same as or different from each other.

2. The organic electronic device of claim 1, wherein the organic electronic device further comprises one or two or more layers selected from the group consisting of a light emitting layer, a hole injection layer, and a hole blocking layer.

3. The organic electronic device of claim 1, wherein the organic electronic device is selected from the group consisting of an organic light emitting device, an organic phosphorescent device, an organic solar cell, an organic photoconductor (OPC), and an organic transistor.

4. The organic electronic device of claim 1, wherein L101 is a direct bond, X1 is a substituted or unsubstituted divalent pyrene group, X2 and X3 are the same as or different from each other, and are each independently an aryl group which is unsubstituted or substituted with a germanium group, and r is 2.

5. The organic electronic device of claim 1, wherein the light emitting layer further comprises a compound represented by the following Chemical Formula A-2:

[Chemical Formula A-2]

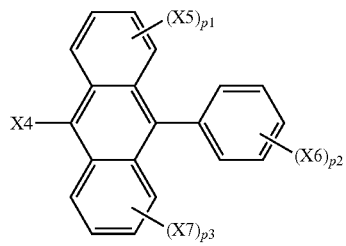

in Chemical Formula A-2,
X4 is a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

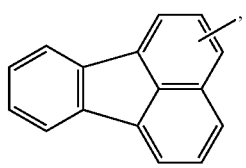

X6 is a phenyl group, a 1-naphtyl group, a 2-naphtyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthracenyl group, a 4'-methylbiphenylyl group, a 4"-t-butyl-p-terphenyl-4-yl group, or a 3-fluoranthenyl group, $X5$ and $X7$ are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, $p2$ is an integer from 1 to 5, $p1$ and $p3$ are each an integer from 1 to 4, and when $p1$ to $p3$ are each 2 or more, each of $X5$, $X6$ and $X7$ is the same as or different from each other.

6. The organic electronic device of claim 5, wherein $X4$ is a 1-naphthyl group, and $X6$ is a 2-naphthyl group.

* * * * *